(12) United States Patent
Lee et al.

(10) Patent No.: US 11,786,745 B2
(45) Date of Patent: Oct. 17, 2023

(54) PLASMA TREATMENT APPARATUS

(71) Applicant: FEAGLE CO., LTD, Yangsan-si (KR)

(72) Inventors: Hyunyoung Lee, Busan (KR);
Jeonghae Choi, Busan (KR); Yeonsuk Song, Busan (KR)

(73) Assignee: FEAGLE CO., LTD, Yangsan-si (KR)

( * ) Notice: Subject to any disclaimer, the term of this patent is extended or adjusted under 35 U.S.C. 154(b) by 1297 days.

(21) Appl. No.: 16/322,104

(22) PCT Filed: Aug. 2, 2016

(86) PCT No.: PCT/KR2016/008479
§ 371 (c)(1),
(2) Date: Jan. 30, 2019

(87) PCT Pub. No.: WO2018/026025
PCT Pub. Date: Feb. 8, 2018

(65) Prior Publication Data
US 2019/0184187 A1   Jun. 20, 2019

(51) Int. Cl.
*H01J 37/32* (2006.01)
*A61N 1/44* (2006.01)
(Continued)

(52) U.S. Cl.
CPC .............. *A61N 1/44* (2013.01); *A61N 1/0408* (2013.01); *A61N 1/08* (2013.01); *B01D 39/20* (2013.01);
(Continued)

(58) Field of Classification Search
CPC .......... A61N 1/08; A61N 1/44; A61N 1/0408; H01J 37/3244; H01J 37/32; H01J 37/32844; H01J 37/32568; B01D 39/20; B01D 53/04; B01D 53/66; B01D 2253/1124; B01D 2257/106; B01D 2259/4533; A61B 2018/00583; A61B 2218/008; A61B 2018/0047; A61B 2218/003; A61B 18/082; A61B 2018/048; A61M 2205/054; A61M 2202/0216; A61M 2210/0606; Y02C 20/30
See application file for complete search history.

(56) References Cited

U.S. PATENT DOCUMENTS

| | | | | |
|---|---|---|---|---|
| 6,086,710 A | * | 7/2000 | Miyashita | ......... H01J 37/32834 156/345.47 |
| 2010/0037820 A1 | * | 2/2010 | Lee | .................... C23C 16/45551 118/719 |
| 2012/0046602 A1 | | 2/2012 | Morfill et al. | |

FOREIGN PATENT DOCUMENTS

| | | |
|---|---|---|
| JP | 63-074141 U | 5/1988 |
| JP | 2002-216933 A | 8/2002 |
| JP | 2012-503508 A | 2/2012 |
| JP | 2013-071105 A | 4/2013 |

(Continued)

OTHER PUBLICATIONS

International Search Report in International Application No. PCT/KR2016/008479, dated May 22, 2017.

*Primary Examiner* — Yuechuan Yu
(74) *Attorney, Agent, or Firm* — PARK, KIM & SUH, LLC

(57) ABSTRACT

Disclosed is a plasma treatment apparatus that includes a cover attached to a body part, a plasma generation unit that generates plasma and provides the plasma to the cover, a gas supply unit that supplies a source gas for generating the plasma to the plasma generation unit, and an exhaust unit that exhausts an exhaust gas from the cover.

19 Claims, 43 Drawing Sheets

(51) Int. Cl.
  *B01D 53/66* (2006.01)
  *B01D 39/20* (2006.01)
  *A61N 1/04* (2006.01)
  *A61N 1/08* (2006.01)
  *B01D 53/04* (2006.01)

(52) U.S. Cl.
  CPC ............. *B01D 53/04* (2013.01); *B01D 53/66* (2013.01); *H01J 37/32* (2013.01); *H01J 37/3244* (2013.01); *H01J 37/32568* (2013.01); *H01J 37/32844* (2013.01); *A61M 2202/0216* (2013.01); *A61M 2205/054* (2013.01); *A61M 2210/0606* (2013.01); *B01D 2253/1124* (2013.01); *B01D 2257/106* (2013.01); *B01D 2259/4533* (2013.01)

(56) References Cited

FOREIGN PATENT DOCUMENTS

| | | |
|---|---|---|
| JP | 2014-505553 A | 3/2014 |
| KR | 10-2004-0049518 A | 6/2004 |
| KR | 10-2008-0004452 A | 1/2008 |
| KR | 10-2012-0063321 A | 6/2012 |
| KR | 10-1171092 B1 | 8/2012 |
| KR | 10-1260893 B1 | 5/2013 |
| KR | 10-2015-0114474 A | 10/2015 |
| KR | 10-1567334 B1 | 11/2015 |
| KR | 10-2016-0072759 A | 6/2016 |
| WO | 03/028179 A1 | 4/2003 |
| WO | 2015/087278 A1 | 6/2015 |
| WO | 2015/087287 A1 | 6/2015 |

\* cited by examiner

Exhaust gas

Exhaust gas

PLASMA TREATMENT APPARATUS

CROSS-REFERENCE TO RELATED APPLICATIONS

This application is the National Stage filing under 35 U.S.C. 371 of International Application No. PCT/KR2016/008479, filed on Aug. 2, 2016, the contents of which are all hereby incorporated by reference herein in their entirety.

TECHNICAL FIELD

Embodiments of the inventive concepts described herein relate to a plasma treatment apparatus.

BACKGROUND

Recently, attempts have been made to treat skin diseases such as acne and an atopic skin disease with plasma. Plasma refers to a state in which matter is divided into electrons with negative charges and ions with positive charges. In plasma, reactivity is maximized so that ionization and recombination of matter are actively performed. Plasma exhibits an effect of improving an affected part through sterilization, skin regeneration, and the like.

However, despite the beneficial effects of plasma, treatment apparatuses using plasma have not been widely studied and developed. As a result, there are not many related products and consumers do not have a wide choice of plasma treatment apparatuses.

SUMMARY

Technical Problem

Embodiments of the inventive concepts provide a plasma treatment apparatus that treats a body part such as skin or a wound using plasma.

Technical Solution

According to an exemplary embodiment, a plasma treatment apparatus includes a cover attached to a body part, a plasma generation unit that generates plasma and provides the plasma to the cover, a gas supply unit that supplies a source gas for generating the plasma to the plasma generation unit, and an exhaust unit that exhausts an exhaust gas from the cover.

The cover may include a mask manufactured in advance to cover a face.

The cover may include a pad manufactured in advance to cover a wound.

The cover may include, at an edge, a sealing part brought into close contact with the body part to seal a space between the cover and the body part.

The cover may further include, on a portion facing the body part, a spacing part for maintaining spacing between the cover and the body part.

The plasma generation unit may be separated from the cover and may provide the plasma to the cover through a tube that connects the plasma generation unit and the cover.

The plasma generation unit may be installed on the cover and may provide the plasma into a space between the cover and the body part.

The plasma generation unit may include opposite electrodes disposed to face each other.

The gas supply unit may include a fan unit that generates an air flow from a space between the opposite electrodes to the space between the cover and the body part.

The plasma generation unit may further include an ozone absorption unit that absorbs ozone between the opposite electrodes and the space between the cover and the body part.

The ozone absorption unit may include a filter with manganese dioxide.

The plasma generation unit may further include a medicine supply unit that supplies a medicine between the opposite electrodes and the space between the cover and the body part.

The medicine supply unit may include a medicine plate with one surface facing the body part and an opposite surface to which the medicine is applied, the medicine plate having a hole through which the plasma mixed with the medicine is sent into the space between the cover and the body part.

A medicine may be applied to at least part of one surface of the cover that faces the body part.

The plasma generation unit may be integrated with the cover and may generate the plasma in a space between the cover and the body part.

The plasma generation unit may include a first electrode formed on an opposite surface of a dielectric material constituting the cover, the opposite surface being opposite to one surface of the dielectric material that faces the body part, and a second electrode formed on the one surface of the dielectric material.

The first electrode may cover at least a partial area on the opposite surface of the dielectric material, and the second electrode on the one surface of the dielectric material may cover part of an area that faces the first electrode.

A power signal may be applied to the first electrode, and the second electrode may be grounded.

The cover may further include a shielding part that shields the first electrode.

The cover may further include a medicine applied to the one surface of the dielectric material.

The medicine may be applied to at least part of a space formed by the one surface of the dielectric material and the second electrode.

The medicine may be applied to a groove formed in at least part of an area on the one surface of the dielectric material that is not covered with the second electrode.

The gas supply unit may supply the source gas to the cover through a gas supply tube.

The gas supply unit may supply air or an inert gas to the plasma generation unit.

The exhaust unit may exhaust air from a space between the cover and the body part before the plasma generation unit generates the plasma after the cover is attached to the body part.

The plasma treatment apparatus may further include a by-product removal unit that removes a by-product from the exhaust gas, a sensor unit that detects whether the body part is sealed by the cover, and a controller that controls the plasma generation unit, depending on whether the body part is sealed or not.

The sensor unit may include at least one contact sensor that is provided on a boundary surface of the cover that makes contact with the body part and that detects whether the boundary surface and the body part are brought into contact with, or separated from, each other.

The controller may stop an operation of the plasma generation unit when the boundary surface and the body part are separated from each other.

The controller may stop the operation of the plasma generation unit when any one of a plurality of contact sensors detects that the boundary surface and the body part are separated from each other.

The controller may restart the operation of the plasma generation unit when the boundary surface and the body part are brought into contact with each other again.

The exhaust unit may include a variable suction pump that takes in the exhaust gas from a space between the cover part and the body part, the variable suction pump being variable in suction pressure.

When the boundary surface and the body part are separated from each other, the controller may raise the suction pressure of the variable suction pump and may stop an operation of the variable suction pump after preset time passes.

The controller may restart the operation of the variable suction pump when the boundary surface and the body part are brought into contact with each other again.

The cover may be configured such that a supply hole through which the cover receives the plasma from the plasma generation unit or receives air from the gas supply unit has a larger area than an exhaust hole through which the exhaust gas is discharged to the exhaust unit.

The cover may further include an exhaust hole adjustment unit that hides or opens part of the exhaust hole to adjust the area of the exhaust hole.

When the boundary surface and the body part are separated from each other, the controller may control the exhaust hole adjustment unit to open part of the exhaust hole to increase the area of the exhaust hole.

When the boundary surface and the body part are brought into contact with each other again, the controller may control the exhaust hole adjustment unit to hide part of the exhaust hole to decrease the area of the exhaust hole.

According to an exemplary embodiment, a plasma treatment apparatus includes a plasma generation unit that generates plasma, a gas supply unit that supplies a source gas for generating the plasma to the plasma generation unit, a path-providing unit that provides a path along which the plasma generation unit moves above a body part, and a driving unit that moves the plasma generation unit along the path-providing unit.

The plasma generation unit may include a first electrode having an empty space through which the source gas passes, a dielectric material that surrounds the first electrode, and a second electrode that surrounds at least part of the dielectric material.

The gas supply unit may supply at least one of argon and helium to the plasma generation unit.

The path-providing unit may include a rail that supports a wheel included in the plasma generation unit.

The path-providing unit may provide a linear path above the body part.

The path-providing unit may provide a closed loop path above the body part.

The path-providing unit may provide, above one or more predetermined intensive care areas of the body part, an intensive care area path in which a first partial path extending in a first direction, a turning path that turns from the first direction to a second direction opposite to the first direction, and a second partial path extending in the second direction are successively connected.

The path-providing unit may provide closed loop paths to a plurality of predetermined intensive care areas of the body part, respectively.

The driving unit may include a wheel 241 included in the plasma generation unit and supported by the path-providing unit and a motor included in the plasma generation unit to rotate the wheel.

The plasma treatment apparatus may further include a medicine spray unit that sprays a medicine while moving along the path-providing unit.

The medicine spray unit following the plasma generation unit may spray the medicine to the body part after the plasma generation unit provides the plasma to the body part.

The plasma treatment apparatus may further include a heater that radiates heat while moving along the path-providing unit.

The heater ahead of the plasma generation unit may transfer heat to the body part before the plasma generation unit provides the plasma to the body part.

The plasma treatment apparatus may further include a medicine mixing unit that has a medicine received therein and is fastened to the plasma generation unit to mix the medicine with the plasma.

The medicine mixing unit may include a fastening part fastened to a nozzle through which the plasma is discharged from the plasma generation unit, a medicine receiving part that receives the medicine, and a discharging part that discharges the plasma mixed with the medicine.

The fastening part may be screw-coupled to the nozzle.

The fastening part may be coupled to a thread formed on the nozzle, the pitch of which is formed in a direction parallel to a nozzle axis.

The medicine receiving part may be formed inside the medicine mixing unit and may receive the medicine in a space formed on a transfer path for transferring the plasma from the nozzle to the discharging part.

The medicine receiving part may be formed inside the medicine mixing unit and may receive the medicine on a transfer path for transferring the plasma from the nozzle to the discharging part.

The transfer path may include a straight tube extending from the nozzle in a straight line.

The transfer path may include a curved tube extending from the nozzle in a curve shape.

The curved tube may extend on a virtual plane where the nozzle and the discharging part are located.

The curved tube may be formed to be wound around a virtual line that connects the nozzle and the discharging part.

The transfer path may include a bent tube extending from the nozzle in a broken line shape.

The bent tube may extend on a virtual plane where the nozzle and the discharging part are located.

The bent tube may be formed to be wound around a virtual line that connects the nozzle and the discharging part.

The medicine receiving part may include, in a portion corresponding to a vertex of the bent tube, a cavity for receiving the medicine.

Advantageous Effects

According to the embodiments of the inventive concept, the plasma treatment apparatuses described above may treat a body part such as skin or a wound using plasma, thereby effectively removing harmful germs in an affected part and promoting regeneration of tissues.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Other advantages and features of the inventive concept, and implementation methods thereof will be clarified through the following embodiments to be described in detail with reference to the accompanying drawings. The inventive concept may, however, be embodied in different forms and should not be construed as being limited to the embodiments set forth herein. Rather, these embodiments are provided so that this disclosure is thorough and complete and fully conveys the scope of the inventive concept to a person skilled in the art to which the inventive concept pertains. Further, the inventive concept is only defined by the appended claims.

Even though not defined, all terms used herein (including technical or scientific terms) have the same meanings as those generally accepted by general technologies in the related art to which the inventive concept pertains. The terms defined in general dictionaries may be construed as having the same meanings as those used in the related art and/or a text of the present application and even when some terms are not clearly defined, they should not be construed as being conceptual or excessively formal.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" used herein specify the presence of stated features or components, but do not preclude the presence or addition of one or more other features or components. In the specification, the term "and/or" indicates each of listed components or various combinations thereof.

Hereinafter, embodiments of the inventive concept will be described in detail with reference to the accompanying drawings.

Figure 1:
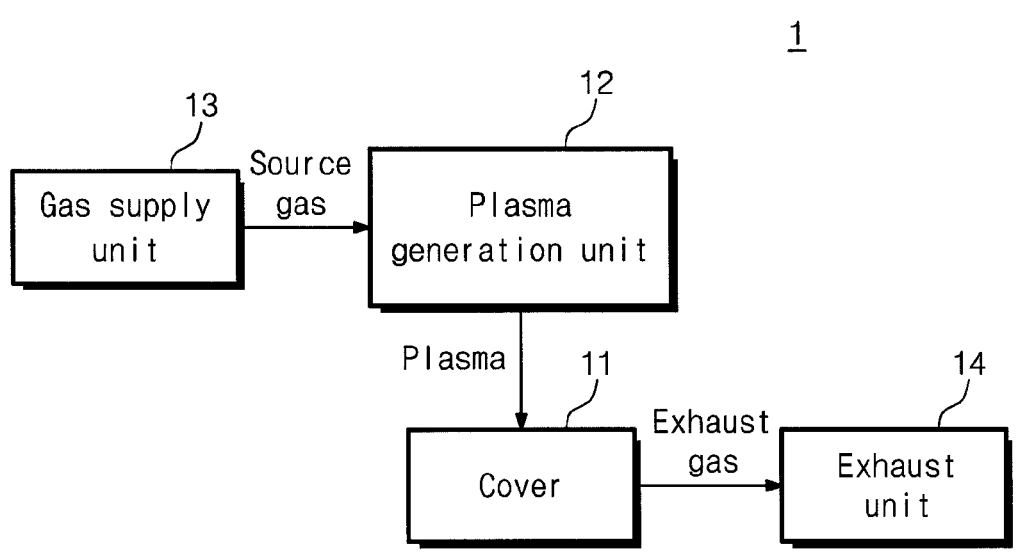
FIG. 1 is a block diagram illustrating a plasma treatment apparatus according to an embodiment of the inventive concept.

FIG. 1 is a block diagram illustrating a plasma treatment apparatus 1 according to an embodiment of the inventive concept.

Referring to FIG. 1, the plasma treatment apparatus 1 includes a cover 11, a plasma generation unit 12, a gas supply unit 13, and an exhaust unit 14. The cover 11 is attached to a body part. The plasma generation unit 12 generates plasma and provides the plasma to the cover 11. The gas supply unit 13 supplies, to the plasma generation unit 12, a source gas for generating the plasma. The exhaust unit 14 exhausts an exhaust gas from the cover 11.

Figure 2:
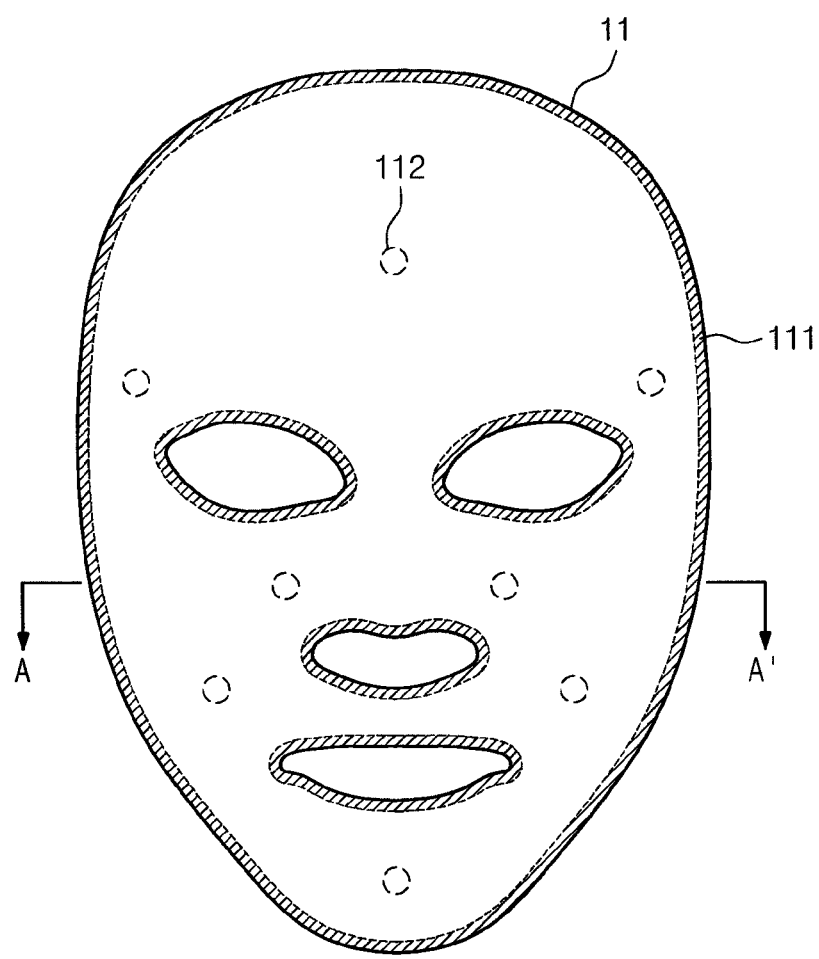
FIGS. 2 to 4 are a front view, a side view, and a sectional view illustrating a cover according to an embodiment of the inventive concept.
Figure 3:
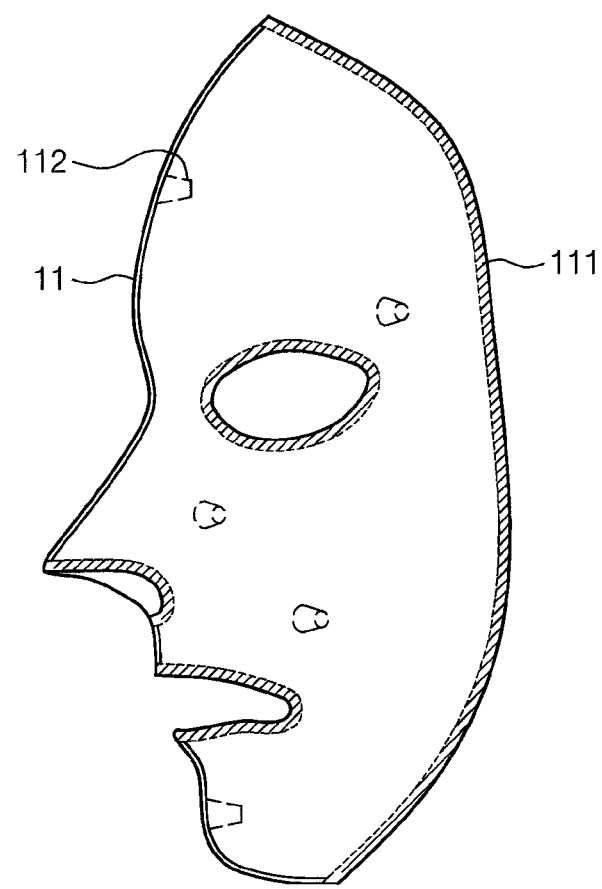
Figure 4:
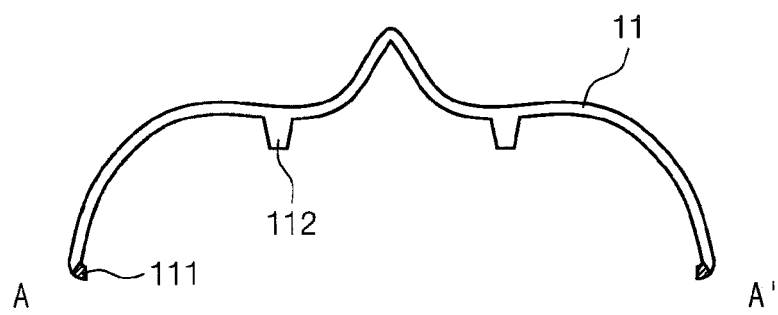

FIGS. 2 to 4 are a front view, a side view, and a sectional view illustrating the cover 11 according to an embodiment of the inventive concept.

According to an embodiment of the inventive concept, the cover 11 may include a mask manufactured in advance to cover a face. That is, the cover 11 in this embodiment may be manufactured in a mask type and may be applied to the face.

The cover 11 may include a sealing part 111 at the edge thereof. Referring to FIGS. 2 to 4, the sealing part 111 may be brought into close contact with the body part at the edge of the cover 11 to seal the space between the cover 11 and the body part.

To seal the space between the cover 11 and the body part, the sealing part 111 may be formed of a soft and flexible material and may be brought into close contact with the body part so that air cannot get in or out. For example, the sealing part 111 may be formed of silicone, rubber, a resin, or the like.

In the case where the cover 11 is manufactured in a mask type, the sealing part 111 may be provided not only at the outer periphery of the mask but also at the edges of various holes (eye holes, a nose hole, a mouth hole, and the like) to seal the space between the mask and the face.

Furthermore, the cover 11 may further include a spacing part 112. The spacing part 112 may be provided on a portion (e.g., the inside) of the cover 11 that faces the body part and may maintain the spacing between the cover 11 and the body part.

As illustrated in FIG. 2, the cover 11 may have a plurality of spacing parts 112 on a portion thereof that faces the body part. As described above, the spacing parts 112 may be provided on predetermined portions on the inside of the cover 11, and therefore the inside of the cover 11 may be kept spaced apart from the body part by a predetermined distance without adhering to the body part during treatment using plasma.

Figure 5:
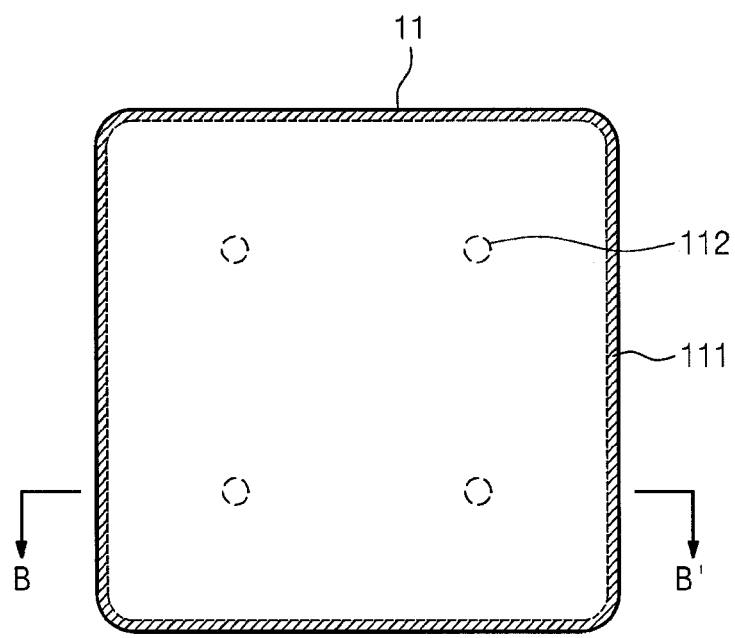
FIGS. 5 and 6 are a front view and a sectional view illustrating a cover according to another embodiment of the inventive concept.
Figure 6:
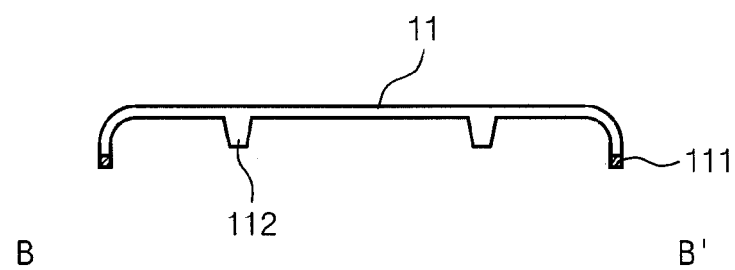

FIGS. 5 and 6 are a front view and a sectional view illustrating the cover 11 according to another embodiment of the inventive concept.

According to another embodiment of the inventive concept, the cover 11 may include a pad manufactured in advance to cover a wound. That is, the cover 11 in this embodiment may be manufactured in a pad type and may be applied to the wound.

Unlike the cover 11 of a mask type, which is manufactured to match a facial contour, the cover 11 according to this embodiment may be manufactured in a flat surface shape or a curved surface shape with a predetermined curvature.

Likewise to the cover 11 of a mask type, the cover 11 of a pad type, as illustrated in FIGS. 5 and 6, may include the sealing part 111 at the edge thereof and may further include the spacing parts 112 on a portion thereof that faces the body part.

Figure 7:
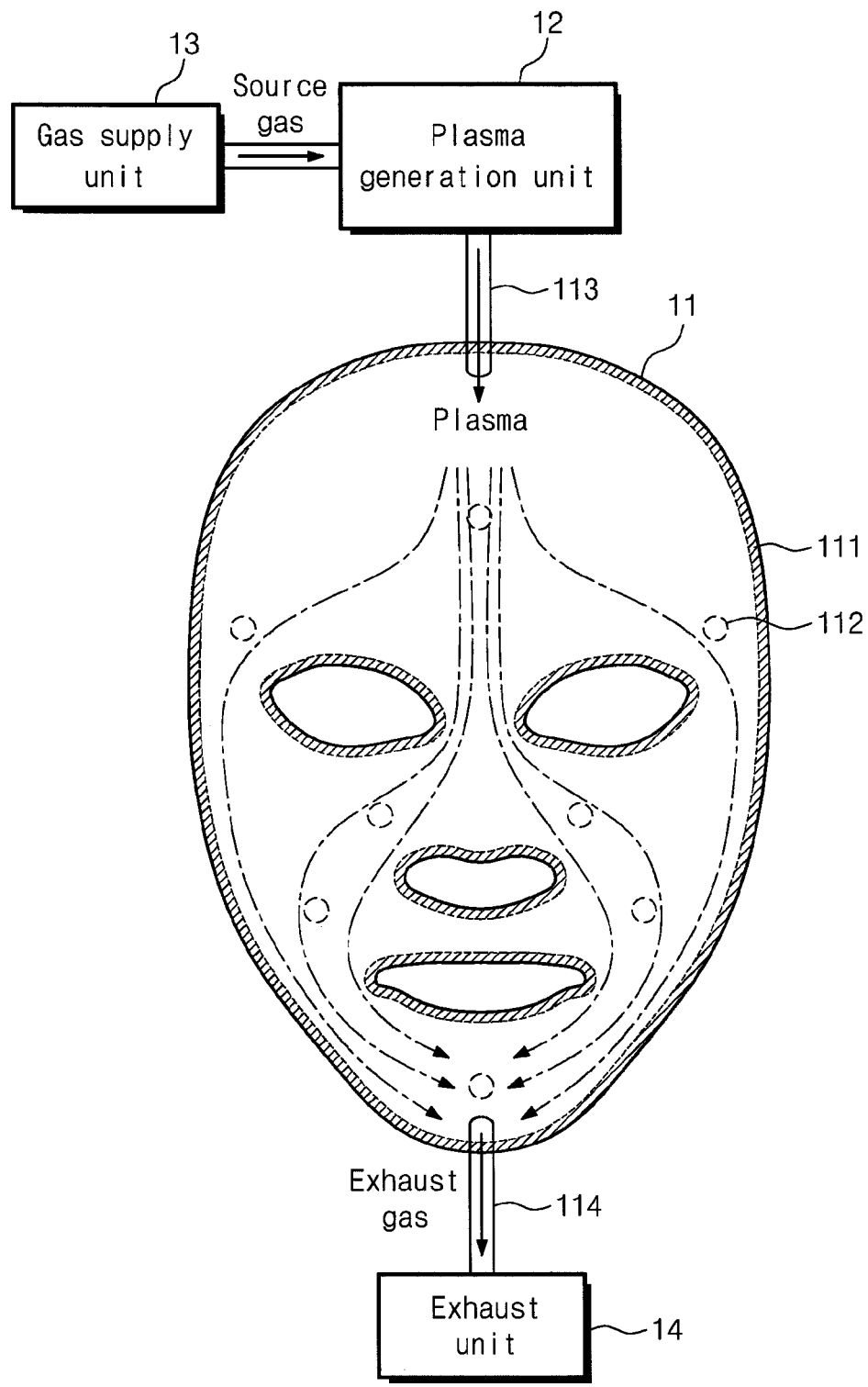
FIG. 7 is a view illustrating an operation of the plasma treatment apparatus according to an embodiment of the inventive concept.

FIG. 7 is a view illustrating an operation of the plasma treatment apparatus 1 according to an embodiment of the inventive concept.

The plasma generation unit 12 generates plasma and provides the plasma to the cover 11. According to an embodiment of the inventive concept, the plasma generation unit 12 may be separated from the cover 11 and may provide the plasma to the cover 11 through a tube 113 that connects the plasma generation unit 12 and the cover 11. That is, the cover 11 and the plasma generation unit 12 in this embodiment may be manufactured as separate modules and may be connected together through the tube 113.

The plasma generation unit 12 may include two opposite electrodes facing each other and may supply power to the opposite electrodes to discharge gas between the electrodes. Plasma generated by the discharge of the gas is transferred to the cover 11 through the tube 113.

At this time, the gas supply unit 13 supplies a source gas to the plasma generation unit 12. According to an embodiment of the inventive concept, the gas supply unit 13 may supply air as the source gas. In this case, the plasma generation unit 12 generates atmospheric plasma. According to another embodiment of the inventive concept, the gas supply unit 13 may supply an inert gas as the source gas. For example, the gas supply unit 13 may supply at least one of argon and helium to the plasma generation unit 12. In this case, the plasma generation unit 12 generates argon or helium plasma.

Furthermore, the exhaust unit 14 exhausts an exhaust gas from the cover 11. By-products may be generated in the process in which the plasma provided from the plasma generation unit 12 to the cover 11 is applied to the body part. For example, the plasma may generate ozone while making contact with air inside the cover 11. In addition, when the plasma generation unit 12 receives air as the source gas, the plasma generation unit 12 may generate and provide plasma and ozone to the cover 11.

The exhaust unit 14 may take in an exhaust gas including the by-products from the cover 11 and may discharge the exhaust gas out of the cover 11. To this end, the exhaust unit 14 may be connected to the cover 11 through an exhaust tube 114 and may include a suction pump to apply a negative pressure to the space between the cover 11 and the body part.

Figure 8:
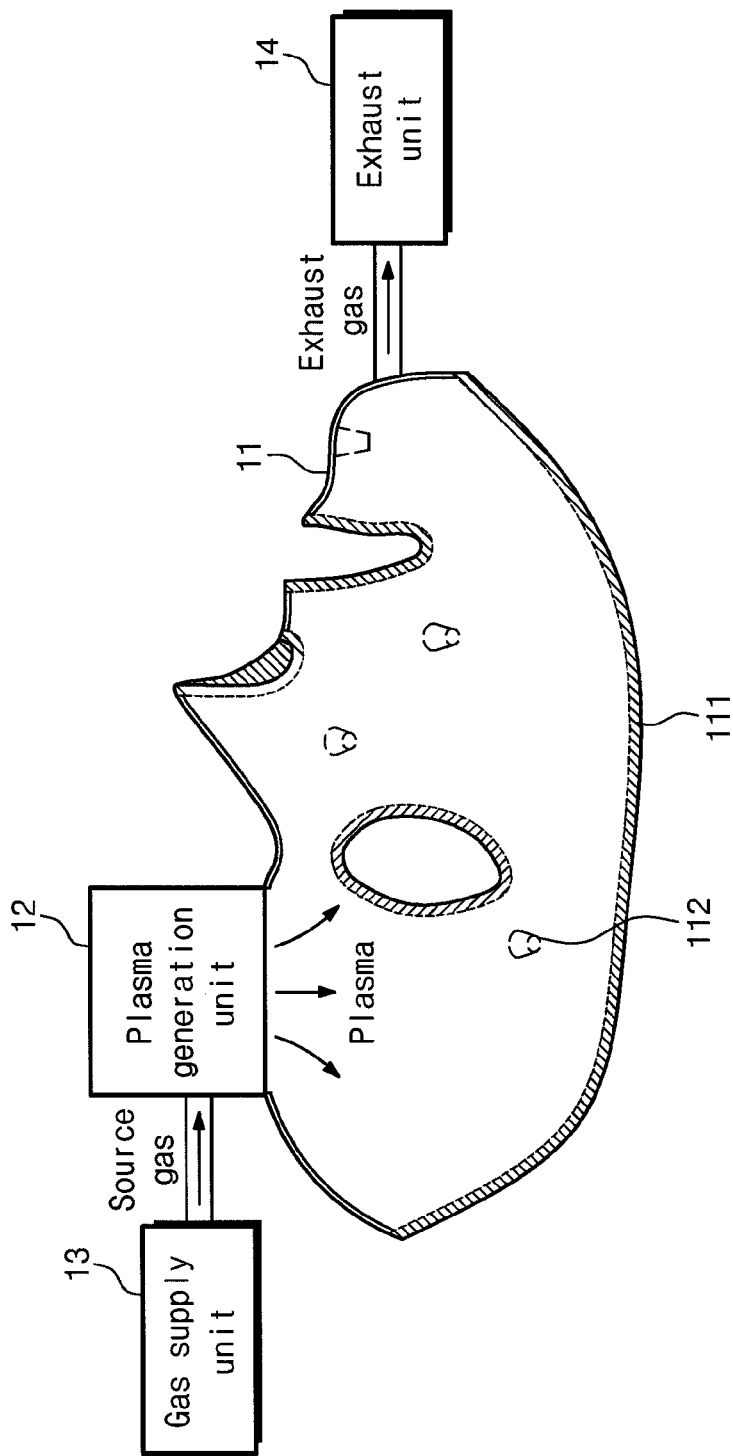
FIG. 8 is a view illustrating a plasma treatment apparatus according to another embodiment of the inventive concept.

FIG. 8 is a view illustrating the plasma treatment apparatus 1 according to another embodiment of the inventive concept.

According to another embodiment of the inventive concept, the plasma generation unit 12 may be installed on the cover 11 and may provide plasma into the space between the cover 11 and a body part. That is, the plasma generation unit 12 in this embodiment is installed on the cover 11 rather than being separated from the cover 11, and therefore the cover 11 and the plasma generation unit 12 are provided together.

While FIG. 8 illustrates an example that the plasma generation unit 12 is installed on a forehead part of the cover 11 of a mask type, the location where the plasma generation unit 12 is installed on the cover 11 is not limited thereto.

As described above, even in this embodiment, the plasma generation unit 12 may include opposite electrodes disposed to face each other. Although not illustrated in the drawing, the plasma generation unit 12 may include a power supply and may supply, to the opposite electrodes, power for generating plasma.

Figure 9:
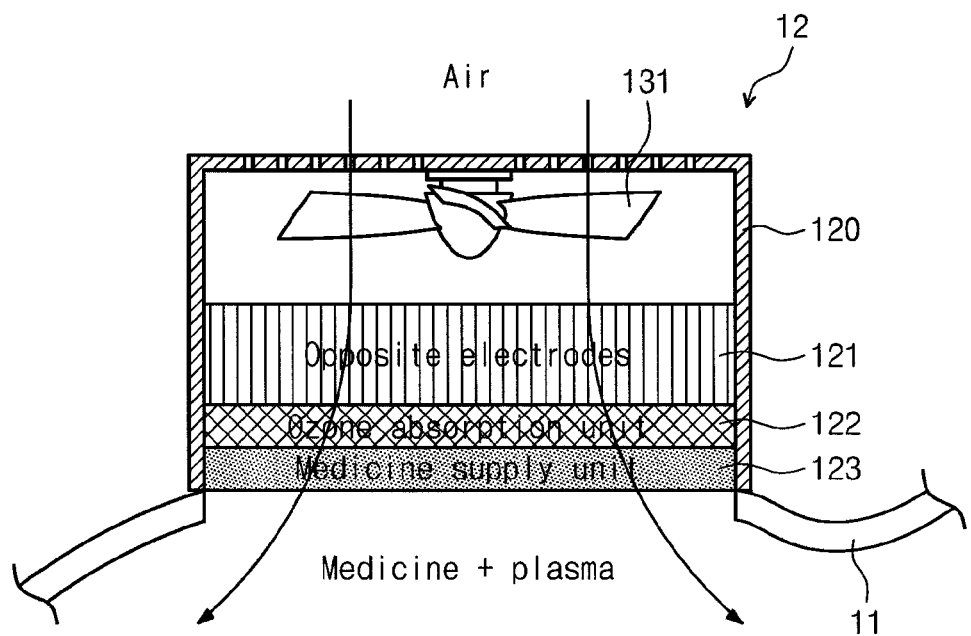
FIG. 9 is a schematic partial sectional view illustrating a plasma generation unit according to another embodiment of the inventive concept.

FIG. 9 is a schematic partial sectional view illustrating the plasma generation unit 12 according to another embodiment of the inventive concept.

As described above, the plasma generation unit 12 in this embodiment is installed on the cover 11 to directly provide plasma to the cover 11 except through a tube.

Furthermore, according to this embodiment, the gas supply unit 13 may also be installed on the cover 11 together with the plasma generation unit 12 rather than being connected to the plasma generation unit 12 through a tube.

Specifically, referring to FIG. 9, the gas supply unit 13 may include a fan unit 131 that generates an air flow from the plasma generation unit 12, that is, the space between opposite electrodes 121 to the space between the cover 11 and the body part.

The fan unit 131 in this embodiment may rotate a fan to supply air to the opposite electrodes 121 as a source gas and move plasma generated by the opposite electrodes 121 inside the cover 11 when power is supplied to the opposite electrodes 121 and discharge occurs in the space between the opposite electrodes 121.

Furthermore, the plasma generation unit 12 may further include an ozone absorption unit 122. The ozone absorption unit 122 is disposed in the space between the opposite electrodes 121, the cover 11, and the body part to absorb ozone.

As described above, in the case where the plasma generation unit 12 receives air as a source gas and generates plasma, the plasma generation unit 12 may further generate ozone as by-products, in addition to the plasma. The plasma generation unit 12 in this embodiment may further include the ozone absorption unit 122 between the opposite electrodes 121 and the cover 11, thereby reducing ozone content in the plasma that is provided to the cover 11.

According to this embodiment, the ozone absorption unit 122 may include a filter having a material for absorbing ozone. For example, the ozone absorption unit 122 may include a filter having manganese dioxide, but the ozone-absorbing material included in the filter is not limited to manganese dioxide.

In addition, the plasma generation unit 12 may further include a medicine supply unit 123. The medicine supply unit 123 is disposed in the space between the opposite electrodes 121, the cover 11, and the body part to supply a medicine.

Figure 10:
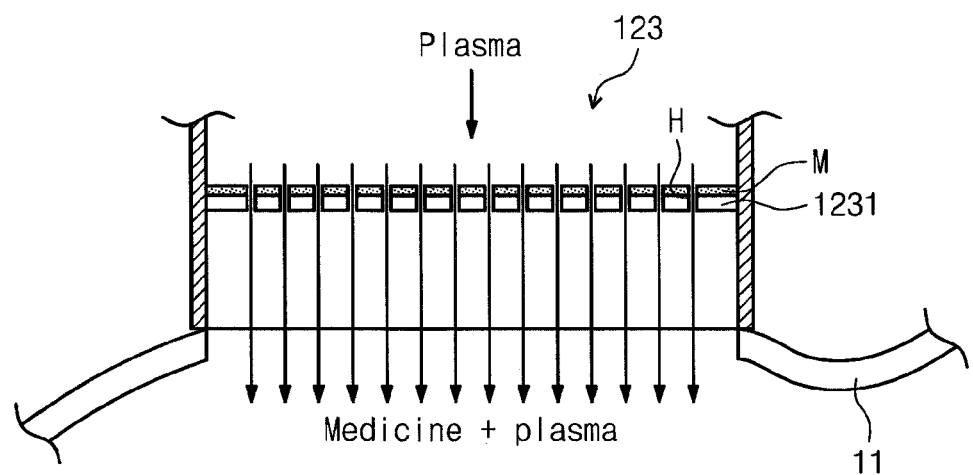
FIGS. 10 and 11 are a sectional view and a plan view illustrating a medicine supply unit according to another embodiment of the inventive concept.
Figure 11:
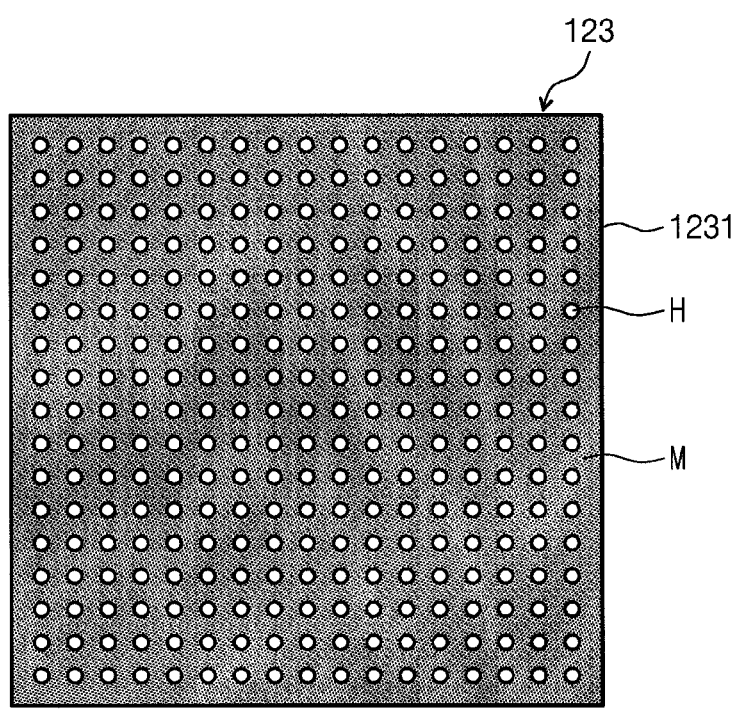

FIGS. 10 and 11 are a sectional view and a plan view illustrating the medicine supply unit 123 according to another embodiment of the inventive concept.

According to this embodiment, the medicine supply unit 123 may include a medicine plate 1231 having holes H formed therethrough, and a medicine M may be applied to a surface of the medicine plate 1231 that is opposite to a surface facing the body part.

For example, referring to FIG. 10, the medicine plate 1231 may be disposed between the opposite electrodes 121 for generating plasma and the cover 11, and the medicine M may be applied to the surface (the upper surface in FIG. 10) of the medicine plate 1231, which is opposite to the surface facing the body part, to form a layer with a predetermined thickness.

As illustrated in FIG. 10, the medicine plate 1231 may have the holes H formed therethrough in the thickness direction and may supply plasma mixed with the medicine M into the space between the cover 11 and the body part. As illustrated in FIG. 11, the holes H may be evenly formed in the medicine plate 1231. Without being limited thereto, however, the holes H may be unevenly formed in the medicine plate 1231.

According to this embodiment, plasma generated by and moving downward from the opposite electrodes 121 may be mixed with the medicine M applied to the medicine plate 1231 and may be supplied to the cover 11 through the holes H, and therefore the effect of the plasma acting on the body part may be further improved.

In the case where the plasma and the medicine M are mixed together and supplied to the body part, the plasma treatment apparatus 1 may enhance the plasma's unique actions such as sterilization and regeneration, thereby maximizing treatment effects by the plasma.

The medicine M in the embodiment of the inventive concept includes any medicine used for treating a body part.

For example, in the case where the plasma treatment apparatus 1 is used for skin care, the medicine supply unit 123 may provide a skin care agent as the medicine M and may mix the skin care agent with plasma. In another example, when the plasma treatment apparatus 1 is used for burn treatment, the medicine supply unit 123 may provide a burn treatment agent as the medicine M and may mix the burn treatment agent with plasma.

In yet another example, the medicine supply unit 123 may provide hydrogen peroxide as the medicine M. For example, gel-type hydrogen peroxide with a predetermined concentration may be applied to the upper surface of the medicine plate 1231. In this case, the plasma treatment apparatus 1 may supply plasma generated by the plasma generation unit 12 to the cover 11 through the medicine supply unit 123 to provide the plasma mixed with the hydrogen peroxide to the body part, thereby further improving sterilization effects of the plasma.

In addition, the medicine M may be applied to at least a portion of a surface of the cover 11 that faces the body part.

Figure 12:
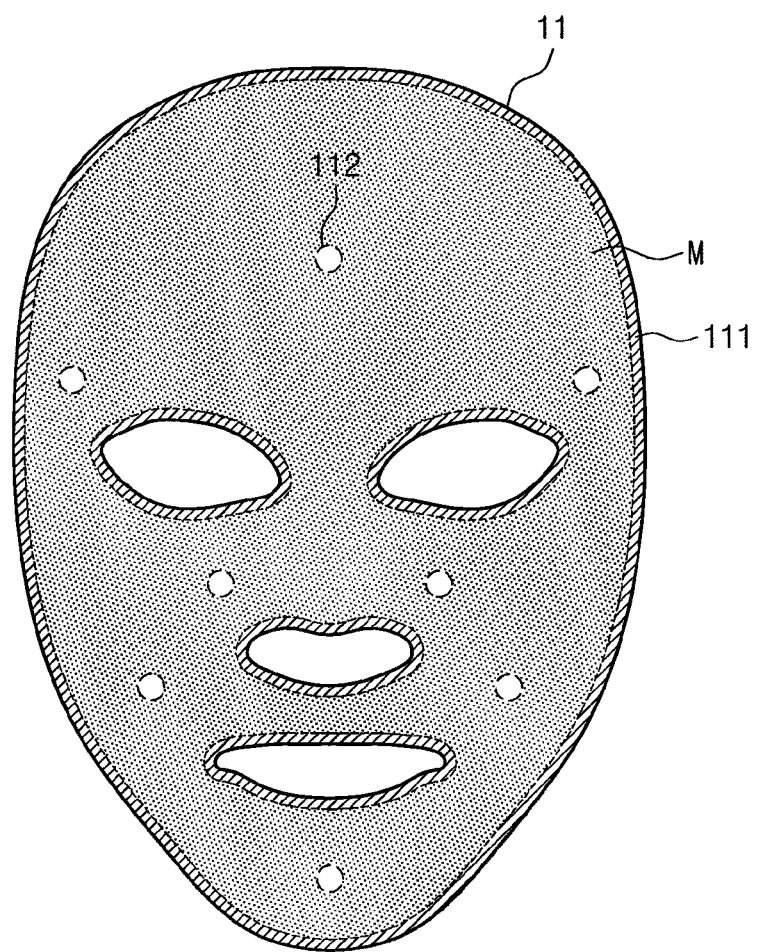
FIG. 12 is a front view illustrating a cover having a medicine applied to one surface thereof according to an embodiment of the inventive concept.

FIG. 12 is a front view illustrating the cover 11 having the medicine M applied to one surface thereof according to an embodiment of the inventive concept.

As illustrated in FIG. 12, the plasma treatment apparatus 1 may have the medicine supply unit 123 included in the plasma generation unit 12, and the medicine M may be applied to one surface (that is, the inside) of the cover 11 that faces a body part.

As a result, plasma supplied from the plasma generation unit 12 may be sufficiently mixed with the medicine M while moving toward the edge of the cover 11 and spreading over the entire area of the cover 11, and therefore enhanced effects of the plasma may be kept during treatment.

Figure 13:
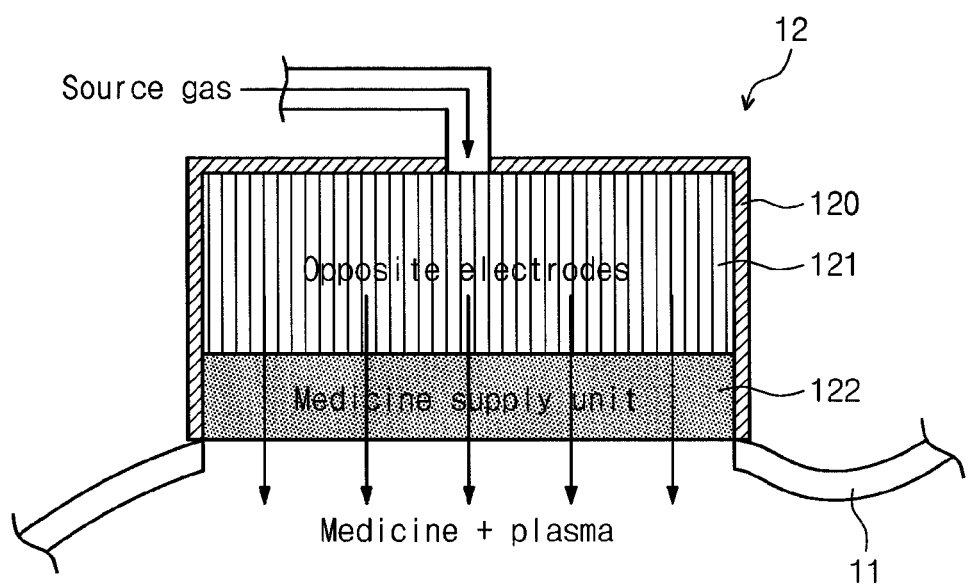
FIG. 13 is a schematic partial sectional view illustrating a plasma generation unit according to yet another embodiment of the inventive concept.

FIG. 13 is a schematic partial sectional view illustrating the plasma generation unit 12 according to yet another embodiment of the inventive concept.

The plasma generation unit 12 illustrated in FIG. 9 has the fan unit 131 that is installed as the gas supply unit 13 to supply air to the opposite electrodes 121.

In contrast, according to yet another embodiment of the inventive concept, the fan unit 131 is not installed in the plasma generation unit 12, but the gas supply unit 13 may be connected to the plasma generation unit 12 through a tube to supply a source gas to the opposite electrodes 121.

This embodiment may be applied in the case where an inert gas such as argon or helium, rather than air, is supplied as the source gas. In the case where an inert gas is used as the source gas, the opposite electrodes 121 do not generate ozone when generating plasma. Therefore, the plasma generation unit 12 may not include the ozone absorption unit 122 and may include only the medicine supply unit 123, unlike in the embodiment of FIG. 9.

In the above-described embodiments, the cover 11 and the plasma generation unit 12 are separately manufactured and connected through the tube 113, or the plasma generation unit 12 is installed on the cover 11.

However, according to yet another embodiment of the inventive concept, the plasma generation unit 12 may be integrated with the cover 11 and may generate plasma in the space between the cover 11 and the body part.

Figure 14:
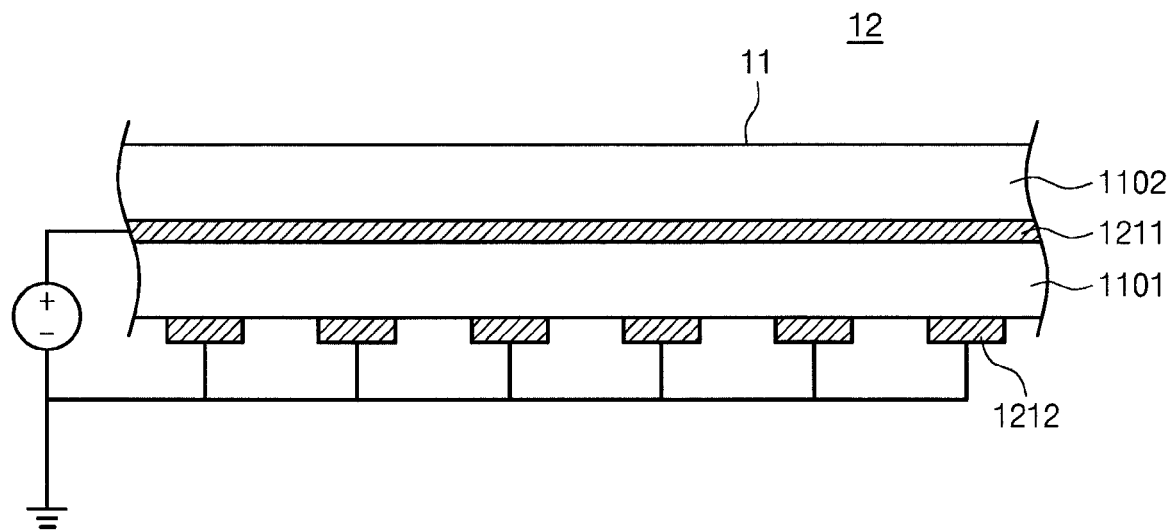
FIGS. 14 and 15 are partial sectional views illustrating a plasma generation unit according to yet another embodiment of the inventive concept.
Figure 15:
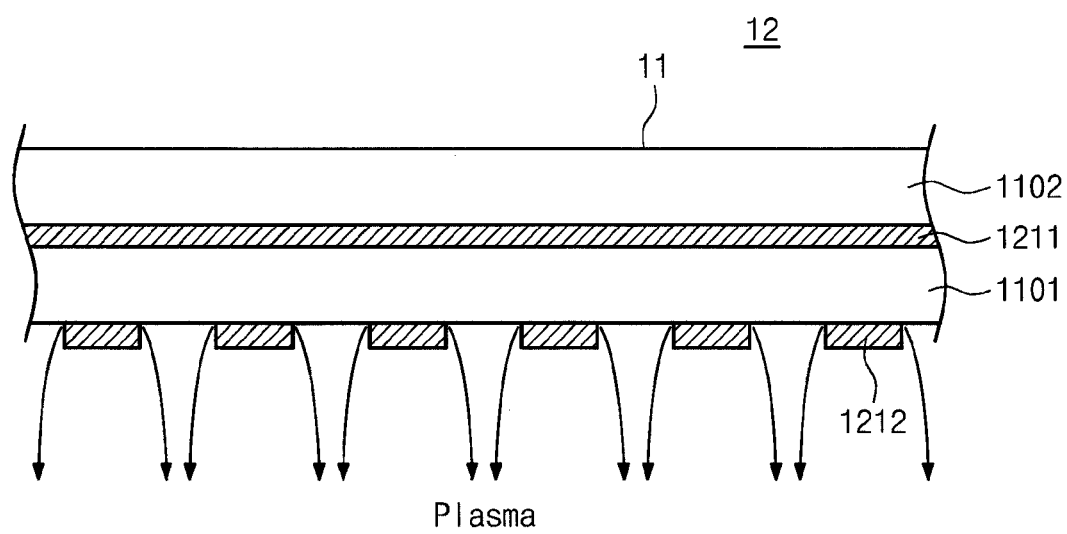

FIGS. 14 and 15 are partial sectional views illustrating the plasma generation unit 12 according to yet another embodiment of the inventive concept.

According to yet another embodiment of the inventive concept, the plasma generation unit 12 may include a first electrode 1211 and a second electrode 1212. The first electrode 1211 may be formed on an opposite surface of a dielectric material 1101 that is opposite to one surface thereof that faces a body part, and the second electrode 1212 may be formed on the one surface of the dielectric material 1101. The dielectric material 1101 may constitute the cover 11. That is, the plasma generation unit 12 in this embodiment may include the first electrode 1211 and the second electrode 1212 facing each other with the dielectric material 1101 therebetween, which constitutes the cover 11.

According to this embodiment, the first electrode 1211 covers at least a partial area on the opposite surface of the dielectric material 1101. The second electrode 1212 on the one surface of the dielectric material 1101 covers part of the area that faces the first electrode 1211.

For example, as illustrated in FIG. 14, the first electrode 1211 is formed to cover all or part of the upper surface of the dielectric material 1101 that constitutes the cover 11. The second electrode 1212 on the lower surface of the dielectric material 1101 covers part of the area that faces the first electrode 1211. As a result, unlike the upper surface of the dielectric material 1101 where the first electrode 1211 is formed, the lower surface of the dielectric material 1101 where the second electrode 1212 is formed is divided into a covered area and an uncovered area.

Furthermore, as illustrated in FIG. 14, a power signal may be applied to the first electrode 1211, and the second electrode 1212 may be grounded. For example, a high-voltage direct current signal or a high-frequency signal may be applied to the first electrode 1211, and the second electrode 1212 may be grounded. Therefore, the first and second electrodes 1211 and 1212 may form a potential difference with the dielectric material 1101 therebetween.

Due to this, as illustrated in FIG. 15, the plasma generation unit 12 may generate plasma with respect to the area on the lower surface of the dielectric material 1101 that is not covered with the second electrode 1212, more specifically, the corner portion where the second electrode 1212 and the dielectric material 1101 meet each other.

Furthermore, according to this embodiment, the cover 11 may further include a shielding part 1102 for shielding the first electrode 1211.

Since the plasma generation unit 12, as described above, applies a high-voltage power signal to the first electrode 1211 to generate plasma, the shielding part 1102 may shield the first electrode 1211 to protect a user of the plasma treatment apparatus 1 from a risk of electric shock. However, the second electrode 1212 facing the body part does not have to be separately shielded since the second electrode 1212 is grounded and therefore there is no risk of electric shock.

Figure 16:
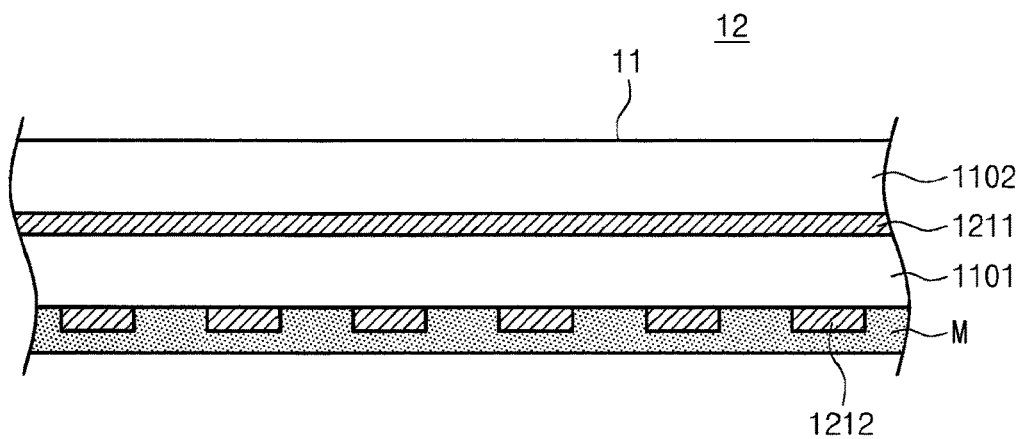
FIG. 16 is a partial sectional view illustrating a plasma generation unit further including a medicine according to an embodiment of the inventive concept.

FIG. 16 is a partial sectional view illustrating the plasma generation unit 12 further including a medicine M according to an embodiment of the inventive concept.

In addition, according to an embodiment of the inventive concept, the cover 11 may further include the medicine M applied to the one surface of the dielectric material 1101.

For example, as illustrated in FIG. 16, the medicine M may be entirely applied to the lower surface of the dielectric material 1101 on which the second electrode 1212 is formed.

Figure 17:
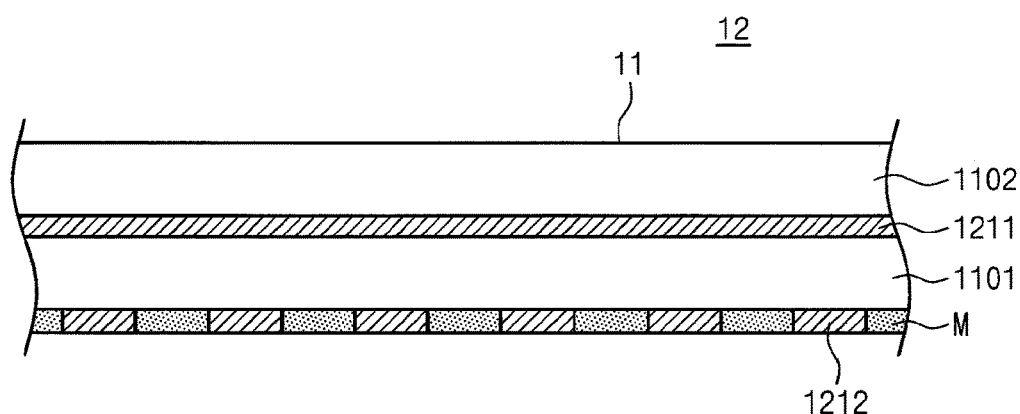
FIG. 17 is a partial sectional view illustrating a plasma generation unit further including a medicine according to another embodiment of the inventive concept.

FIG. 17 is a partial sectional view illustrating the plasma generation unit 12 further including a medicine M according to another embodiment of the inventive concept.

According to another embodiment of the inventive concept, the medicine M may be applied to the space formed by the one surface of the dielectric material 1101 and the second electrode 1212.

For example, as illustrated in FIG. 17, the medicine M is not entirely applied to the lower surface of the dielectric material 1101 on which the second electrode 1212 is formed, but may fill at least part of the space surrounded by the lower surface of the dielectric material 1101 and the side surfaces of the second electrode 1212.

Figure 18:
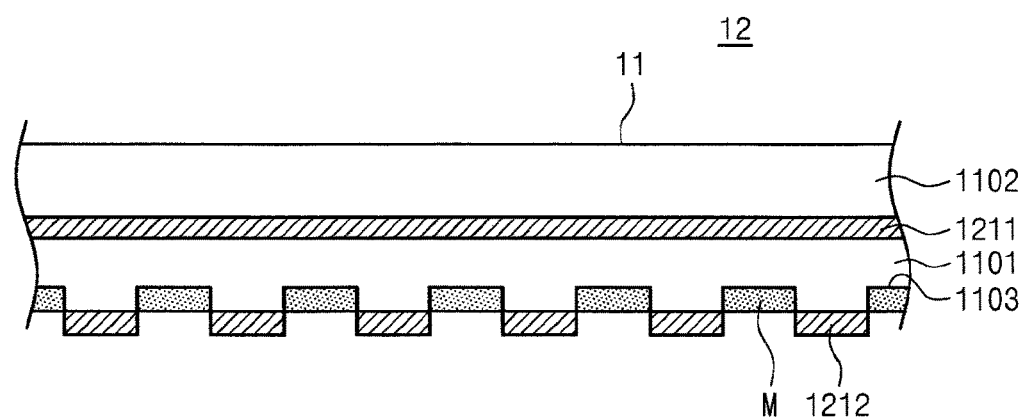
FIG. 18 is a partial sectional view illustrating a plasma generation unit further including a medicine according to yet another embodiment of the inventive concept.

FIG. 18 is a partial sectional view illustrating the plasma generation unit 12 further including a medicine M according to yet another embodiment of the inventive concept.

According to yet another embodiment of the inventive concept, the medicine M may be applied to a groove 1103 formed in at least part of the area on the one surface of the dielectric material 1101 that is not covered with the second electrode 1212.

For example, as illustrated in FIG. 18, the dielectric material 1101 may further include the groove 1103 formed in all or part of the remaining area other than the area on the lower surface of the dielectric material 1101 that is covered with the second electrode 1212. The groove 1103 may be filled with the medicine M.

As described above, the plasma generation unit 12 may further include the medicine M on the one surface of the dielectric material 1101, on which the second electrode 1212 is formed, thereby further increasing treatment effects of plasma on a body part.

Figure 19:
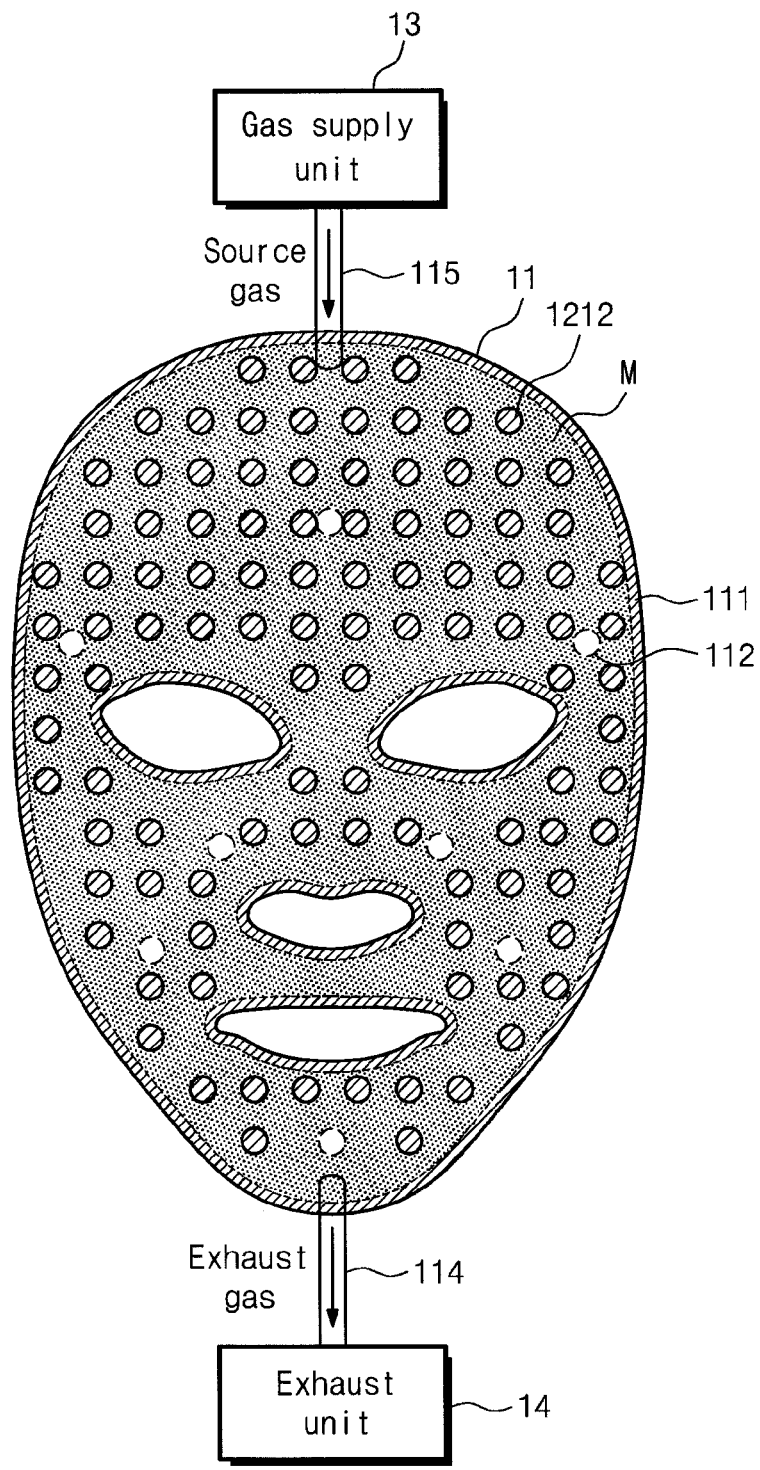
FIG. 19 is a view illustrating an operation of a plasma treatment apparatus according to yet another embodiment of the inventive concept.

FIG. 19 is a view illustrating an operation of the plasma treatment apparatus 1 according to yet another embodiment of the inventive concept.

In the embodiment in which the plasma generation unit 12 is integrated with the cover 11, the gas supply unit 13 may supply a source gas to the cover 11 through a gas supply tube 115.

For example, the gas supply unit 13 may supply air to the cover 11 through the gas supply tube 115. In this case, the plasma generation unit 12 generates atmospheric plasma. In another example, the gas supply unit 13 may supply at least one of argon and helium to the cover 11 through the gas supply tube 115. In this case, the plasma generation unit 12 generates argon or helium plasma.

As in the other embodiments, the plasma generation unit 12 may generate plasma and may provide the plasma to the cover 11, and ozone may be generated as by-products. The exhaust unit 14 may take in an exhaust gas including the by-products from the cover 11 and may discharge the exhaust gas out of the cover 11.

Although not illustrated in the drawing, the plasma treatment apparatus 1 may further include a controller. The controller may control operations of the plasma generation unit 12, the gas supply unit 13, and the exhaust unit 14 to enable a user to perform treatment on a body part using the plasma treatment apparatus 1.

Figure 20:
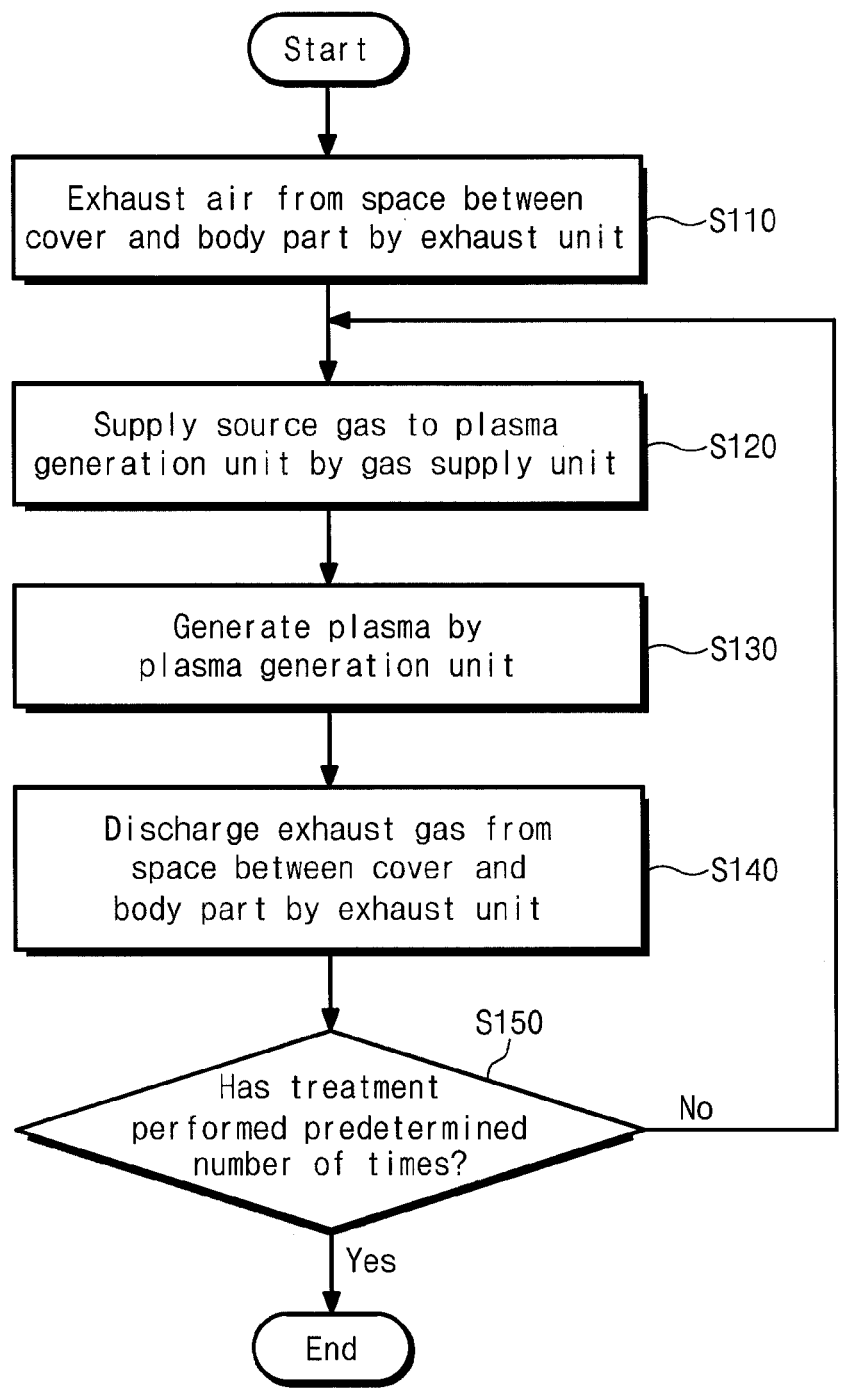
FIG. 20 is a flowchart illustrating a process in which a controller controls an operation of a plasma treatment apparatus according to an embodiment of the inventive concept.

FIG. 20 is a flowchart illustrating a process in which the controller controls an operation of the plasma treatment apparatus 1 according to an embodiment of the inventive concept.

Referring to FIG. 20, the controller may control to perform process S110 of exhausting air from the space between the cover 11 and a body part by the exhaust unit 14, process S120 of supplying a source gas to the plasma generation unit 12 by the gas supply unit 13, process S130 of generating plasma by the plasma generation unit 12, and process S140 of discharging an exhaust gas from the space between the cover 11 and the body part by the exhaust unit 14.

According to this embodiment, the exhaust unit 14 exhausts air from the space between the cover 11 and the body part before the plasma generation unit 12 generates plasma after the cover 11 is attached to the body part.

Due to this, a negative pressure may be applied to the space between the cover 11 and the body part, and therefore the cover 11 may be brought into close contact with the body part. Furthermore, the negative pressure applied to the space between the cover 11 and the body part may open hair follicles of the body part, thereby further increasing beauty effects by plasma when the plasma treatment apparatus 1 is used for skin care. In addition, since pressure is decreased in the space between the cover 11 and the body part, plasma firing voltage may be lowered, which may lead to an improvement in plasma generation efficiency.

Figure 21:
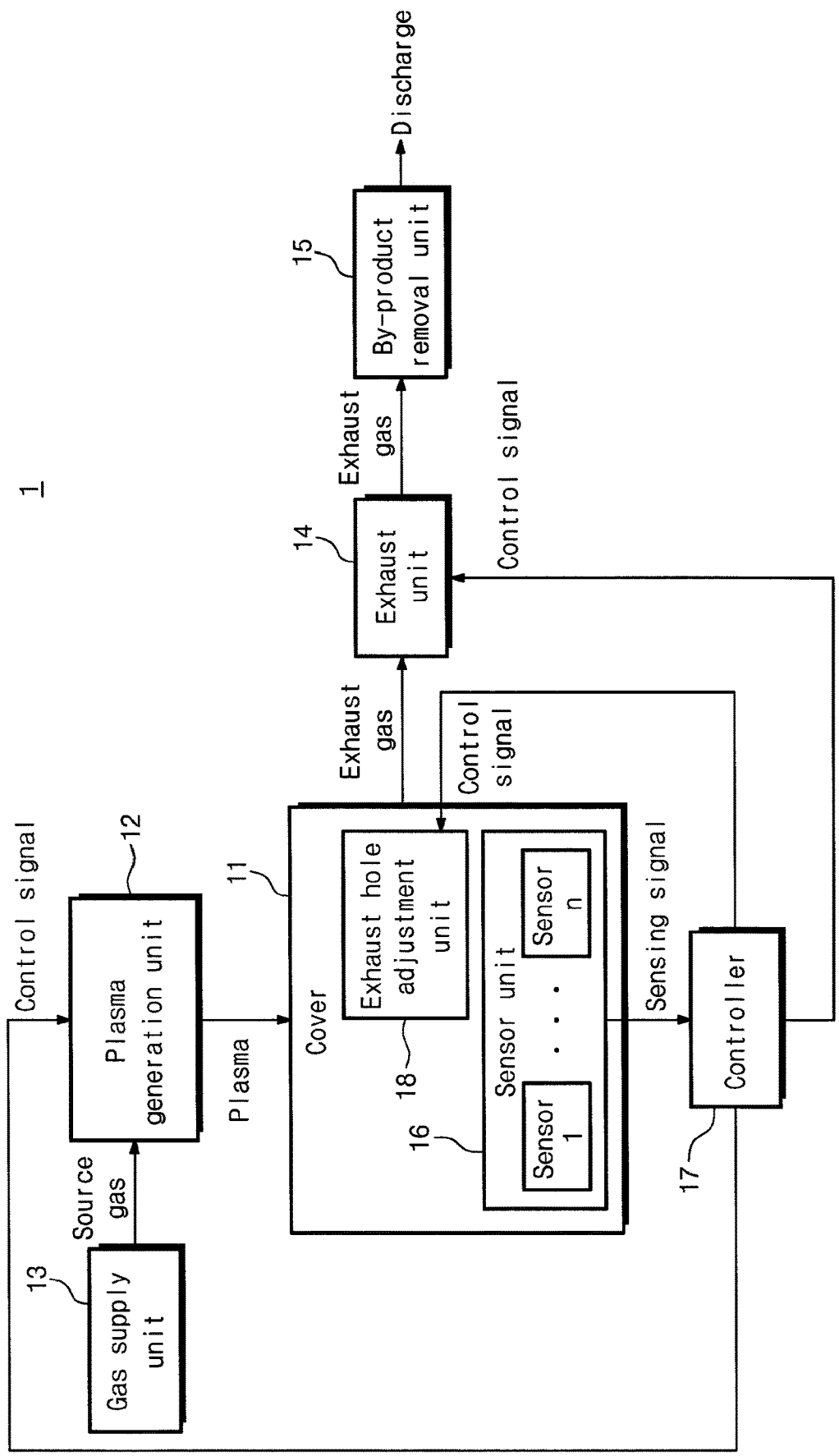
FIG. 21 is a block diagram illustrating a plasma treatment apparatus according to another embodiment of the inventive concept.

FIG. 21 is a block diagram illustrating the plasma treatment apparatus 1 according to another embodiment of the inventive concept.

Referring to FIG. 21, the plasma treatment apparatus 1 may further include a by-product removal unit 15, a sensor unit 16, and a controller 17.

The by-product removal unit 15 removes by-products from an exhaust gas. The sensor unit 16 detects whether a body part is sealed by the cover 11. The controller 17 controls the plasma generation unit 12, depending on whether the body part is sealed or not.

The by-product removal unit 15 may include a filter that removes by-products included in the exhaust gas while allowing the exhaust gas to pass through.

According to an embodiment, the by-product removal unit 15 may include an ozone removal filter that removes ozone from the exhaust gas. That is, a by-product removed by the by-product removal unit 15 in this embodiment is ozone.

The ozone removal filter may have a material for absorbing ozone. For example, the ozone removal filter may have manganese dioxide as an ozone absorbing material, but the material included in the filter is not limited to manganese dioxide.

By-products removed from the exhaust gas by the by-product removal unit 15 are not limited to ozone. The by-product removal unit 15 may remove various other by-products harmful to human bodies or an environment.

The by-product removal unit 15 may filter the exhaust gas passing through the exhaust unit 14 to remove by-products. In other words, the exhaust gas exhausted from the cover 11 may pass through the by-product removal unit 15 past the exhaust unit 14 and may be discharged out of the plasma treatment apparatus 1.

However, according to another embodiment, the by-product removal unit 15 may be disposed between the cover 11 and the exhaust unit 14. For example, the by-product removal unit 15 may be installed in an exhaust tube that connects the cover 11 and the exhaust unit 14. In another example, the by-product removal unit 15 may be installed in an exhaust hole included in the cover 11 and may remove by-products in an exhaust gas leaving the cover 11.

While FIG. 21 illustrates an example that the exhaust gas passing through the exhaust unit 14 and the by-product removal unit 15 is discharged out of the plasma treatment apparatus 1, the exhaust gas may be supplied to the plasma generation unit 12 again. In other words, the exhaust unit 14 may supply the exhaust gas to the plasma generation unit 12 to allow the exhaust gas to circulate in the plasma treatment apparatus 1.

In this case, the plasma treatment apparatus 1 may form a closed system. Therefore, even though by-products are slightly included in the exhaust gas passing through the by-product removal unit 15, a user is less likely to be exposed to the by-products while the apparatus is in operation since the exhaust gas is not discharged to the outside.

Figure 22:
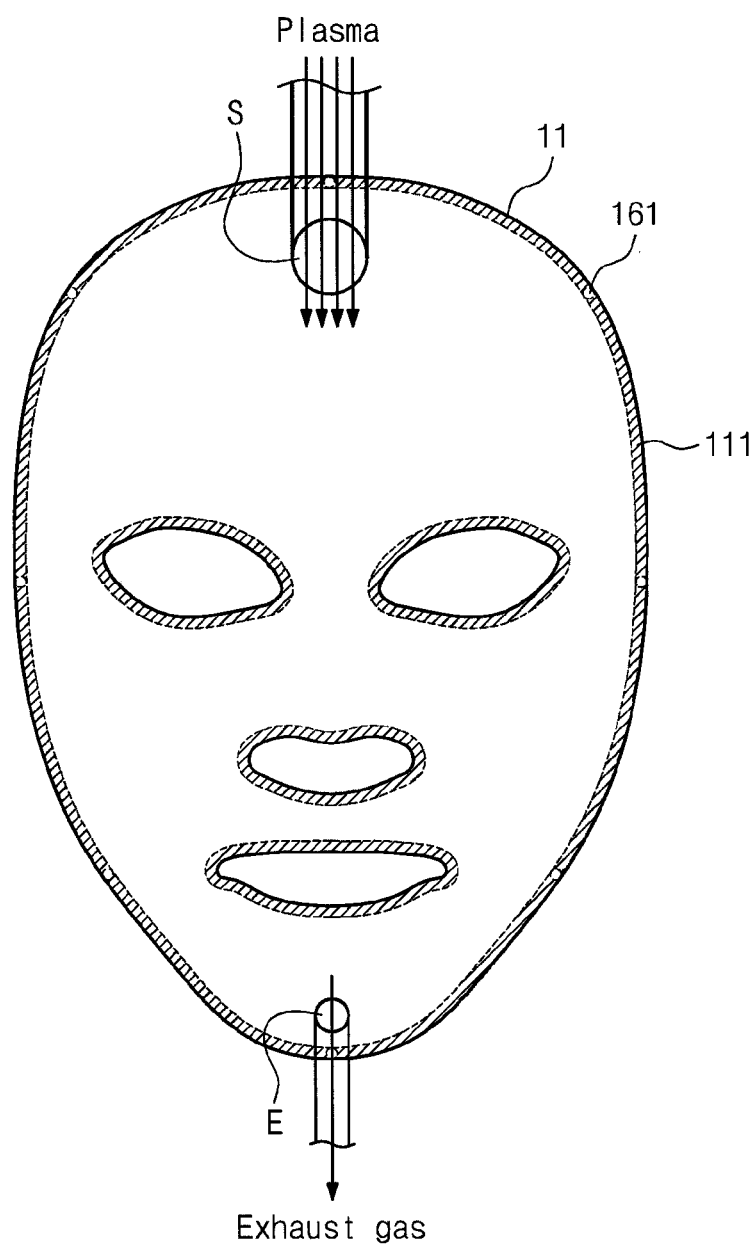
FIG. 22 is a front view illustrating a cover in a plasma treatment apparatus according to another embodiment of the inventive concept, with a boundary surface and a body part making contact with each other.
Figure 23:
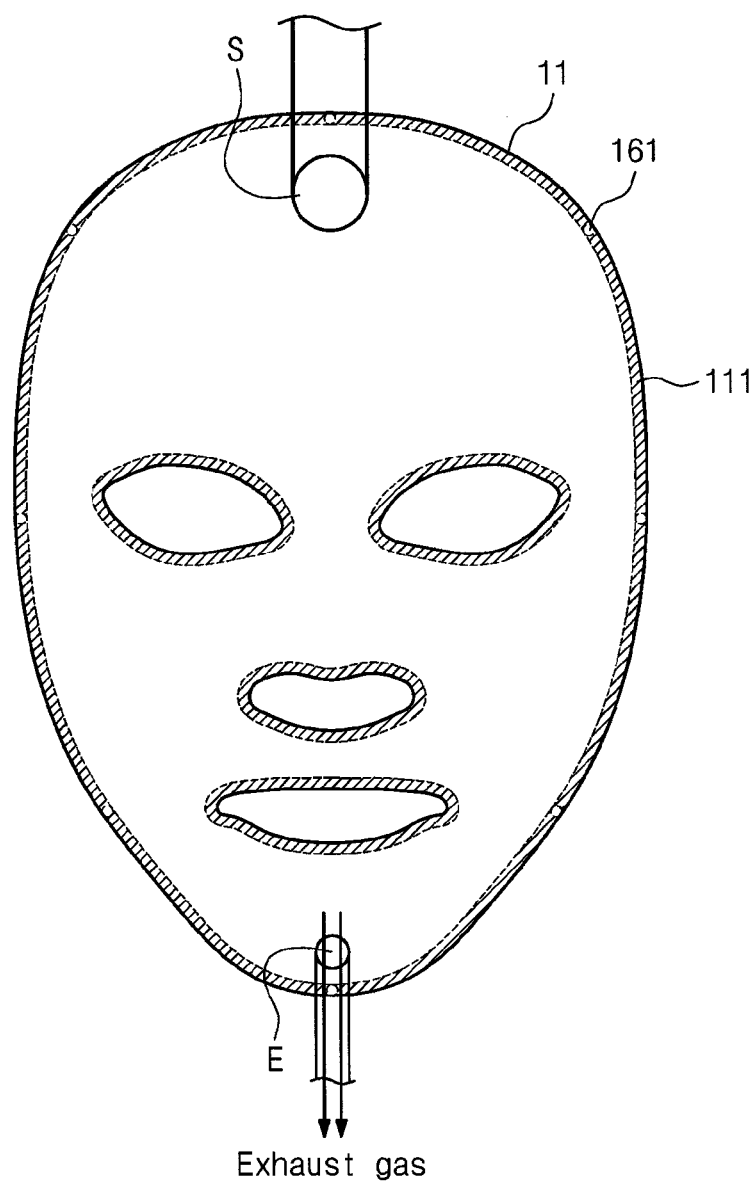
FIG. 23 is a front view illustrating the cover in the plasma treatment apparatus according to another embodiment of the inventive concept, with the boundary surface and the body part separated from each other.

FIG. 22 is a front view illustrating the cover 11 in the plasma treatment apparatus 1 according to another embodiment of the inventive concept, with a boundary surface and a body part making contact with each other. FIG. 23 is a front view illustrating the cover 11 in the plasma treatment apparatus 1 according to another embodiment of the inventive concept, with the boundary surface and the body part separated from each other.

The sensor unit 16 detects whether the body part is sealed by the cover 11.

According to an embodiment, the sensor unit 16 may include at least one contact sensor 161 that is provided on the boundary surface of the cover 11 making contact with the body part and that detects whether the boundary surface and the body part are brought into contact with, or separated from, each other.

For example, referring to FIGS. 22 and 23, the at least one contact sensor 161 may be provided on the boundary surface (e.g., the sealing part 111) of the cover 11 that makes contact with the body part. When the boundary surface of the cover 11 makes contact with the body part, the contact sensor 161 may detect the contact and may output an electrical signal corresponding to the contact.

According to another embodiment, the sensor unit 16 may include at least one pressure sensor provided on the boundary surface of the cover 11. The pressure sensor may detect pressure exerted on the pressure sensor and may convert the pressure into an electrical signal. The pressure sensor may include, for example, a strain gauge, a load cell, or the like.

In the case where the pressure sensor is used to detect whether the body part is sealed or not, when the pressure detected by the pressure sensor is lower than a preset threshold value, it may be determined that the body part is not sealed, and when the pressure is higher than or equal to the threshold value, it may be determined that the body part is sealed.

The controller 17 controls the plasma generation unit 12, depending on whether the body part is sealed or not.

According to an embodiment, the controller 17 may stop an operation of the plasma generation unit 12 in the case where the body part is not sealed.

For example, in the case where the contact sensor 161 is used to detect whether the body part is sealed or not, the controller 17, as illustrated in FIG. 23, may stop an operation of the plasma generation unit 12 to stop the supply of plasma to the cover 11 when the contact sensor 161 detects the separation of the boundary surface and the body part.

In the case where a plurality of contact sensors 161 are installed on the cover 11, the controller 117 may stop an operation of the plasma generation unit 12 when any one of the plurality of contact sensors 161 detects the separation of the boundary surface and the body part. In other words, when any one of the plurality of contact sensors 161 detects the separation of the boundary surface and the body part, the plasma generation unit 12 stops operating.

In addition, the controller 17 may restart the operation of the plasma generation unit 12 in the case where the body part is sealed again.

For example, in the case where the contact sensor 161 detects the contact between the boundary surface and the body part again, the controller 17, as illustrated in FIG. 22, may restart the operation of the plasma generation unit 12 to start the supply of plasma to the cover 11 again.

Figure 24:
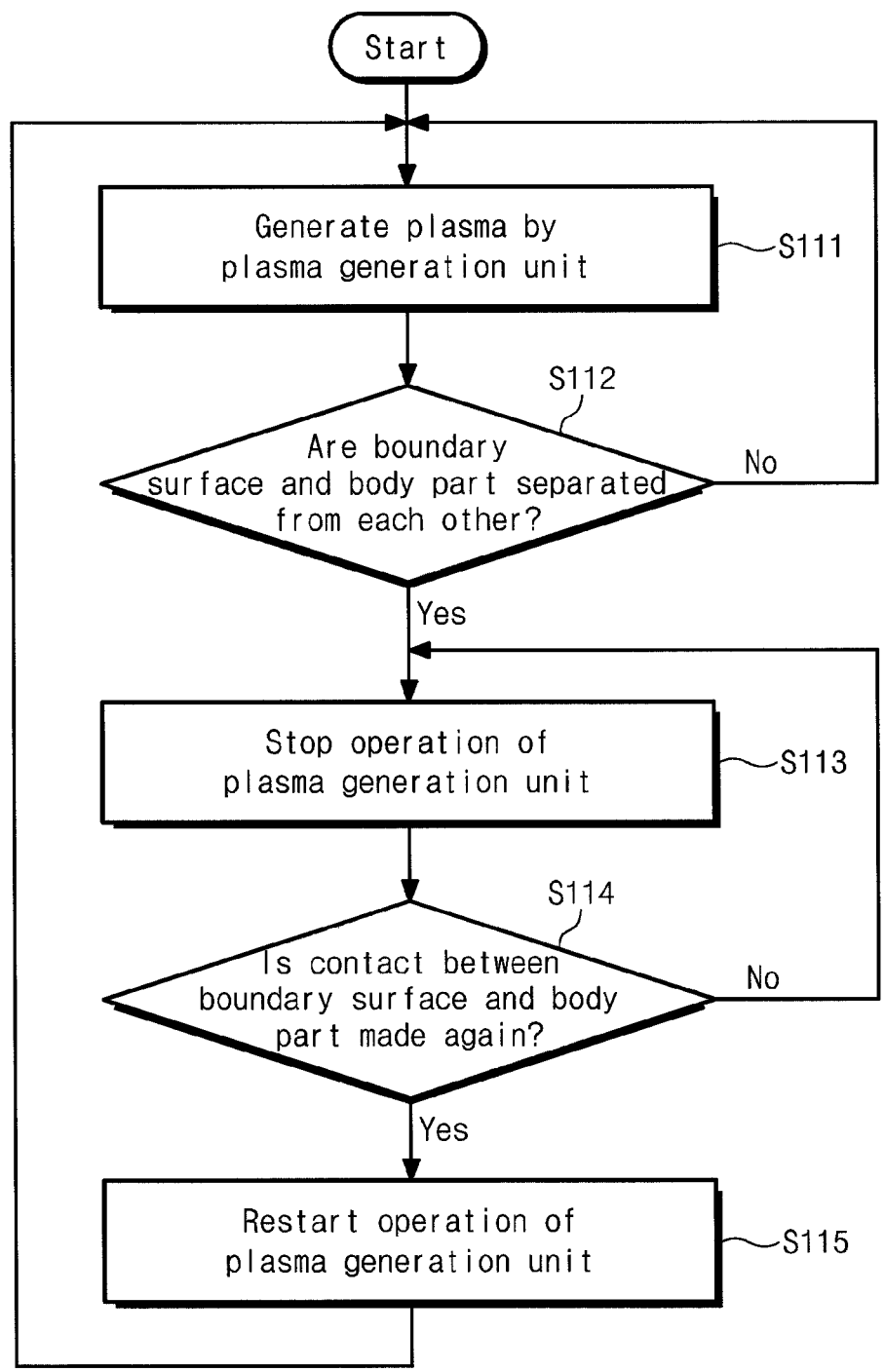
FIG. 24 is a flowchart illustrating a process in which a controller controls a plasma generation unit according to another embodiment of the inventive concept.

FIG. 24 is a flowchart illustrating a process in which the controller 17 controls the plasma generation unit 12 according to another embodiment of the inventive concept.

Referring to FIG. 24, the controller 17 may control to perform process S111 of generating plasma by the plasma generation unit 12, process S113 of stopping an operation of the plasma generation unit 12 when a boundary surface and a body part are separated from each other (Y in Process S112), and process S115 of restarting the operation of the plasma generation unit 12 when the boundary surface and the body part make contact with each other again (Y in Process S114).

As described above, the controller 17 may control the plasma generation unit 12, depending on whether the body part is sealed or not. Accordingly, in the case where the body part is not sealed by the cover 11 and therefore an exhaust gas is likely to be leaked, the plasma generation unit 12 may stop operating to stop generation of plasma and by-products generated along with the plasma.

According to another embodiment of the inventive concept, the controller 17 may control the exhaust unit 14, depending on whether the body part is sealed or not.

According to this embodiment, the exhaust unit 14 may include a suction pump that takes in an exhaust gas from the space between the cover 11 and the body part. The suction pump may be a variable suction pump that is variable in suction pressure.

In the case where the body part is not sealed, the controller 17 may raise the suction pressure of the variable suction pump. Thereafter, the controller 17 may stop an operation of the variable suction pump after preset time passes.

For example, when the contact sensor 161 detects that the boundary surface and the body part are separated from each other, the controller 17 may temporarily raise the suction pressure of the variable suction pump and may stop an operation of the variable suction pump after preset time passes.

In addition, the controller 17 may restart the operation of the variable suction pump in the case where the body part is sealed again.

For example, in the case where the contact sensor 161 detects contact between the boundary surface and the body part again, the controller 17 may restart the operation of the variable suction pump.

Figure 25:
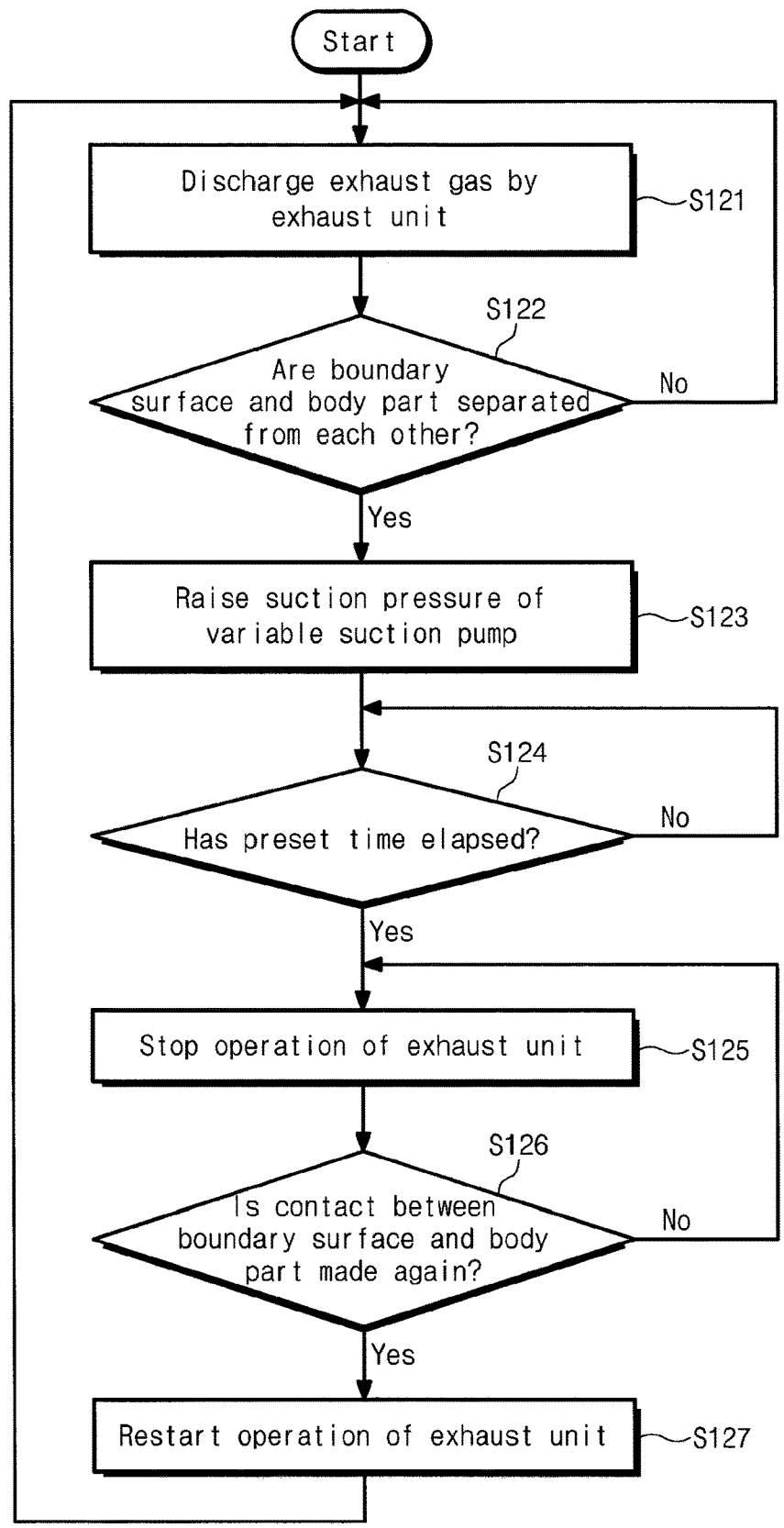
FIG. 25 is a flowchart illustrating a process in which a controller controls an exhaust unit according to another embodiment of the inventive concept.

FIG. 25 is a flowchart illustrating a process in which the controller 17 controls the exhaust unit 14 according to another embodiment of the inventive concept.

Referring to FIG. 25, the controller 17 may control to perform process S121 of exhausting an exhaust gas by the exhaust unit 14, process S123 of raising the suction pressure of a variable suction pump included in the exhaust unit 14 in the case where a boundary surface and a body part are separated from each other (Y in Process S122), process S125 of stopping an operation of the exhaust unit 14 after preset time passes (Y in Process S124), and process S127 of restarting the operation of the exhaust unit 14 in the case where the boundary surface and the body part make contact with each other again (Y in Process S126).

The controller 17 may control the exhaust unit 14 and the variable suction pump included therein, depending on whether the body part is sealed or not. As a result, in the case where the body part is not sealed by the cover 11 and therefore the exhaust gas is likely to be leaked, the suction pressure of the variable suction pump may be instantaneously raised to rapidly discharge by-products present in the space between the cover 11 and the body part from the cover 11.

According to an embodiment of the inventive concept, the cover 11 may be configured such that the area of a supply hole S through which plasma is supplied from the plasma generation unit 12 into the cover 11 is greater than the area of an exhaust hole E through which the exhaust gas is discharged to the exhaust unit 14.

For example, referring to FIGS. 22 and 23, the area of the supply hole S that is formed in the cover 11 and through which plasma generated by the plasma generation unit 12 passes may be greater than the area of the exhaust hole E that is formed in the cover 11 and through which the exhaust gas passes. In other words, the area of the exhaust hole E through which the exhaust gas is discharged from the cover 11 is smaller than the area of the supply hole S through which plasma is introduced into the cover 11.

In the case where, as illustrated in FIG. 19, the plasma generation unit 12 is integrated with the cover 11 and plasma is generated in the space between the cover 11 and the body part, the area of the supply hole S through which a source gas is supplied from the gas supply unit 13 may be greater than the area of the exhaust hole E.

According to this embodiment, time during which plasma stays in the cover 11 may be increased, and therefore the plasma may sufficiently interact with the body part, thereby effectively performing treatment on the body part.

Figure 26:
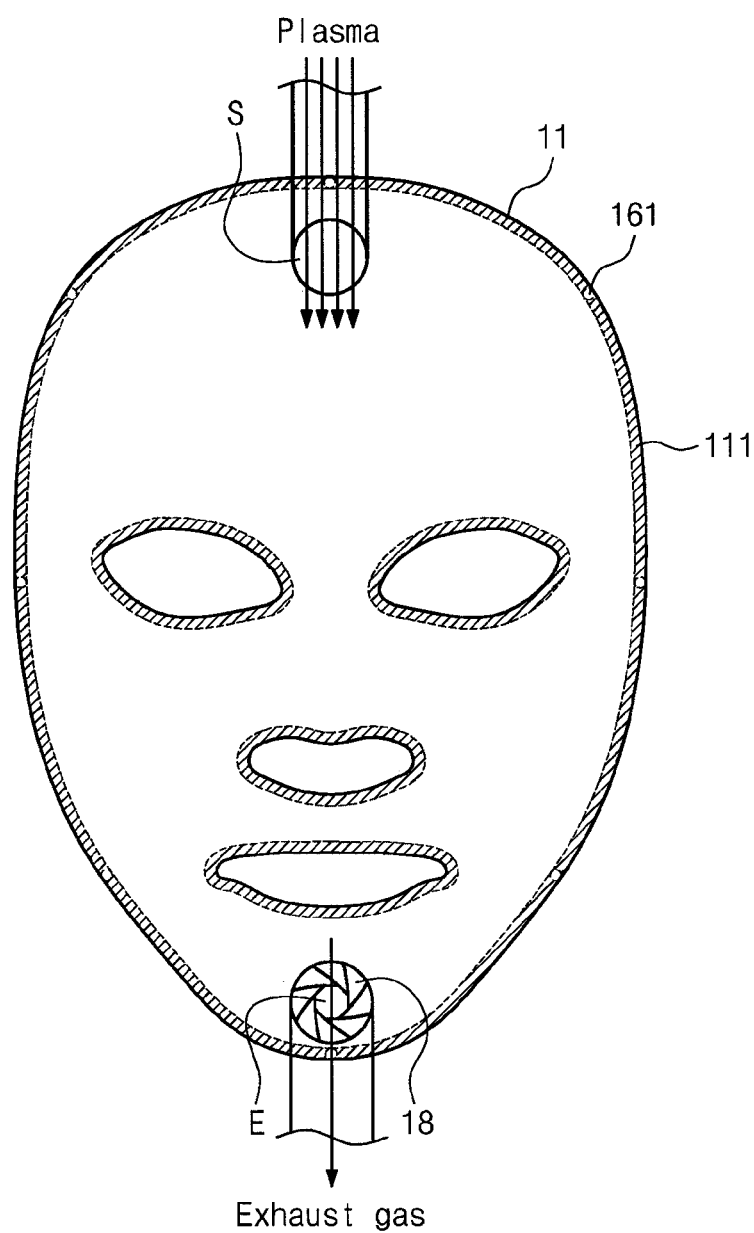
FIG. 26 is a front view illustrating a cover in a plasma treatment apparatus according to yet another embodiment of the inventive concept, with a boundary surface and a body part making contact with each other.

FIG. 26 is a front view illustrating the cover 11 in the plasma treatment apparatus 1 according to yet another embodiment of the inventive concept, with a boundary surface and a body part making contact with each other. FIG.

27 is a front view illustrating the cover 11 in the plasma treatment apparatus 1 according to yet another embodiment of the inventive concept, with the boundary surface and the body part separated from each other.

According to yet another embodiment of the inventive concept, the cover 11 may further include an exhaust hole adjustment unit 18 that hides or opens a portion of the exhaust hole E to adjust the area of the exhaust hole E.

For example, as illustrated in FIG. 26, the exhaust hole adjustment unit 18 may hide a portion of the exhaust hole E when plasma is supplied into the cover 11 to perform treatment on the body part. At this time, the exhaust hole adjustment unit 18 installed in the exhaust hole E may hide a portion of the entire area of the exhaust hole E such that the area of the exhaust hole E is smaller than the area of the supply hole S as described above.

According to this embodiment, in the case where the body part is not sealed, the controller 17 may control the exhaust hole adjustment unit 18 such that a portion of the exhaust hole E is opened to increase the area of the exhaust hole E.

Figure 27:
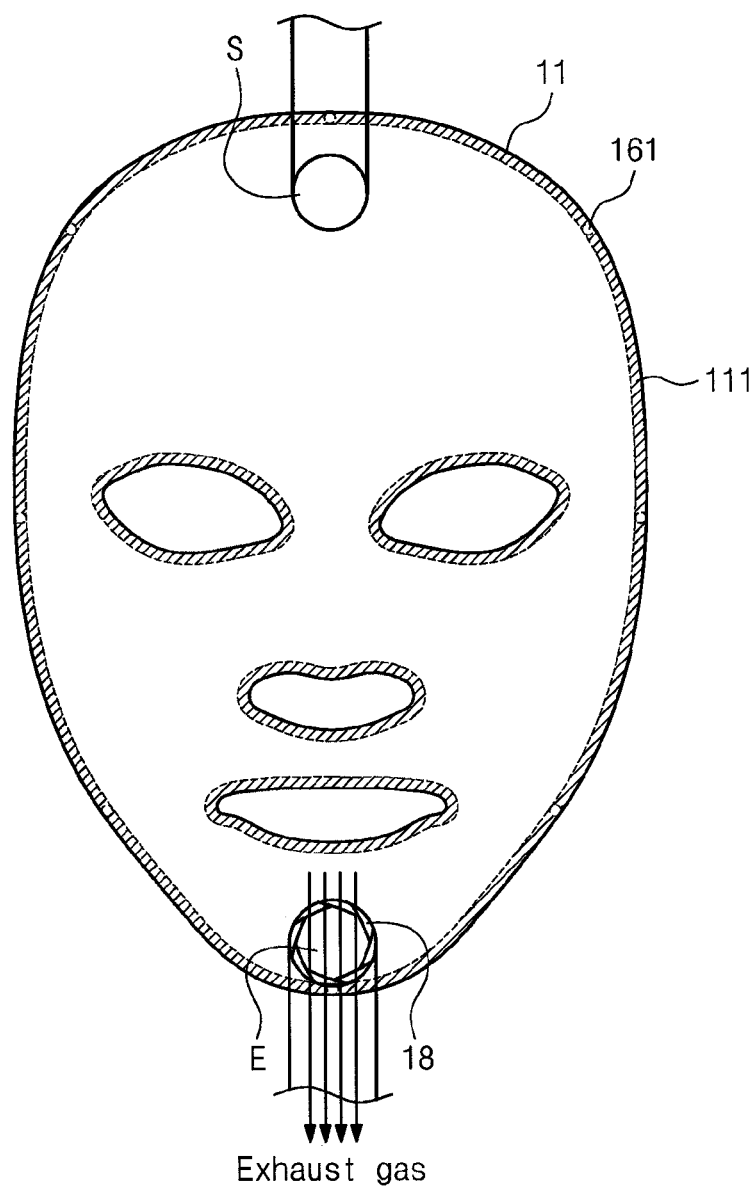
FIG. 27 is a front view illustrating the cover in the plasma treatment apparatus according to yet another embodiment of the inventive concept, with the boundary surface and the body part making contact with each other.

For example, in the case where the boundary surface of the cover 11 and the body part are separated from each other and therefore the body part is not sealed, the controller 17, as illustrated in FIG. 27, may control the exhaust hole adjustment unit 18 to open a portion of the exhaust hole E hidden by the exhaust hole adjustment unit 18 to increase the area of the exhaust hole E.

To adjust the area of the exhaust hole E depending on whether the body part is sealed or not, the exhaust hole adjustment unit 18 may include a screen that is movable on a plane where the exhaust hole E is located, like a shutter of a camera. The screen may be operated by an actuator that operates according to a control signal of the controller 17.

In addition, in this embodiment, in the case where the body part is sealed again, the controller 17 may control the exhaust hole adjustment unit 18 such that a portion of the exhaust hole E is hidden again to decrease the area of the exhaust hole E.

For example, in the case where the boundary surface of the cover 11 and the body part make contact with each other again and therefore the body part is sealed, the controller 17, as illustrated in FIG. 26, may operate the exhaust hole adjustment unit 18 to hide a partial area of the exhaust hole E again to decrease the area of the exhaust hole E.

Figure 28:
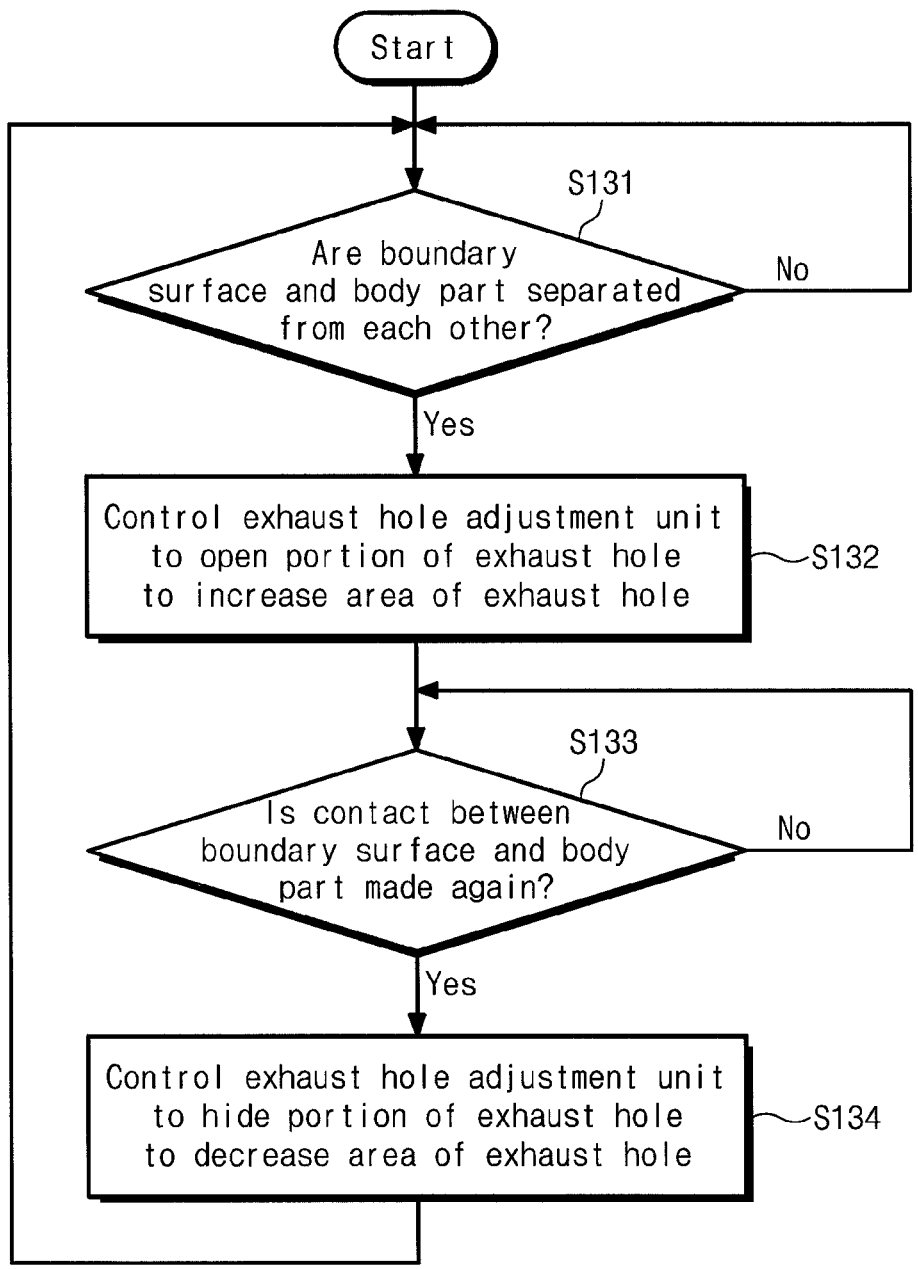
FIG. 28 is a flowchart illustrating a process in which a controller controls an exhaust hole adjustment unit according to yet another embodiment of the inventive concept.

FIG. 28 is a flowchart illustrating a process in which the controller 17 controls the exhaust hole adjustment unit 18 according to yet another embodiment of the inventive concept.

Referring to FIG. 28, the controller 17 may control to perform process S132 of controlling the exhaust hole adjustment unit 18 to open a portion of the exhaust hole E to increase the area of the exhaust hole E when a boundary surface and a body part are separated from each other (Y in Process S131) and process S134 of controlling the exhaust hole adjustment unit 18 to hide a portion of the exhaust hole E to decrease the area of the exhaust hole E when the boundary surface and the body part make contact with each other again (Y in Process S133).

The controller 17 may control the exhaust hole adjustment unit 18 to adjust the area of the exhaust hole E, depending on whether the body part is sealed or not. As a result, in the case where the body part is not sealed by the cover 11 and therefore an exhaust gas is likely to be leaked, the area of the exhaust hole E may be increased to increase the amount of exhaust gas discharged from the cover 11 by the exhaust unit 14, thereby rapidly discharging by-products remaining in the space between the cover 11 and the body part from the cover 11.

The above-described plasma treatment apparatus 1 relates to a closed-type plasma treatment system that covers and seals a body part with the cover 11 such as a mask or a pad and then treats the body part with plasma or plasma and medicine. Hereinafter, an open-type plasma treatment system will be described that treats a body part with plasma or plasma and medicine, with the body part not being sealed.

Figure 29:
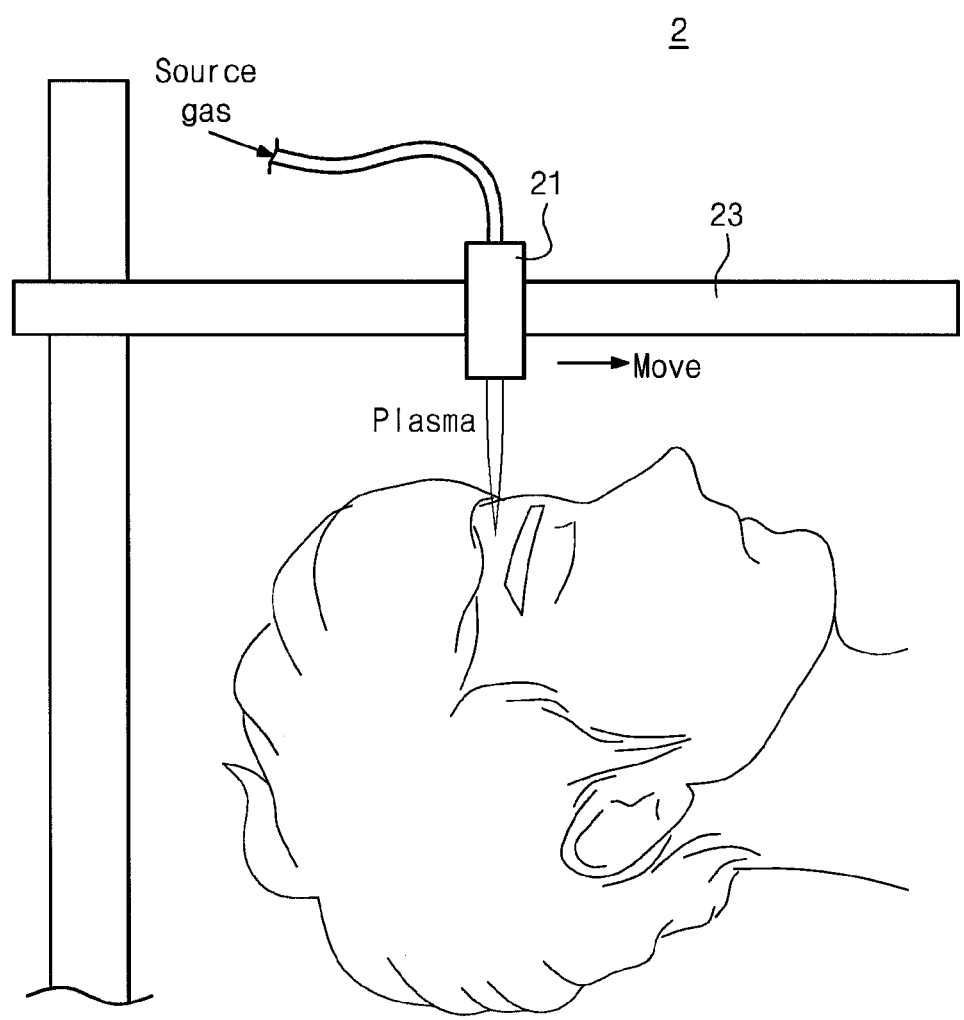
FIG. 29 is a side view illustrating a plasma treatment apparatus according to an embodiment of the inventive concept.

FIG. 29 is a side view illustrating a plasma treatment apparatus 2 according to an embodiment of the inventive concept.

The plasma treatment apparatus 2 according to an embodiment of the inventive concept includes a plasma generation unit 21, a gas supply unit (not illustrated), a path-providing unit 23, and a driving unit 24.

The plasma generation unit 21 generates plasma. The gas supply unit supplies, to the plasma generation unit 21, a source gas for generating the plasma. The path-providing unit 23 provides a path along which the plasma generation unit 21 moves above a body part. The driving unit 24 moves the plasma generation unit 21 along the path-providing unit 23.

The plasma generation unit 21 may discharge the source gas with high voltage to divide gas in a discharging space into electrons and ions. The source gas excited into a plasma state by the plasma generation unit 21 is sprayed from a nozzle of the plasma generation unit 21 and provided to the body part.

A face is illustrated in FIG. 29 as an example of the body part to be treated with plasma. Without being limited thereto, however, the body part includes various body parts.

Figure 30:
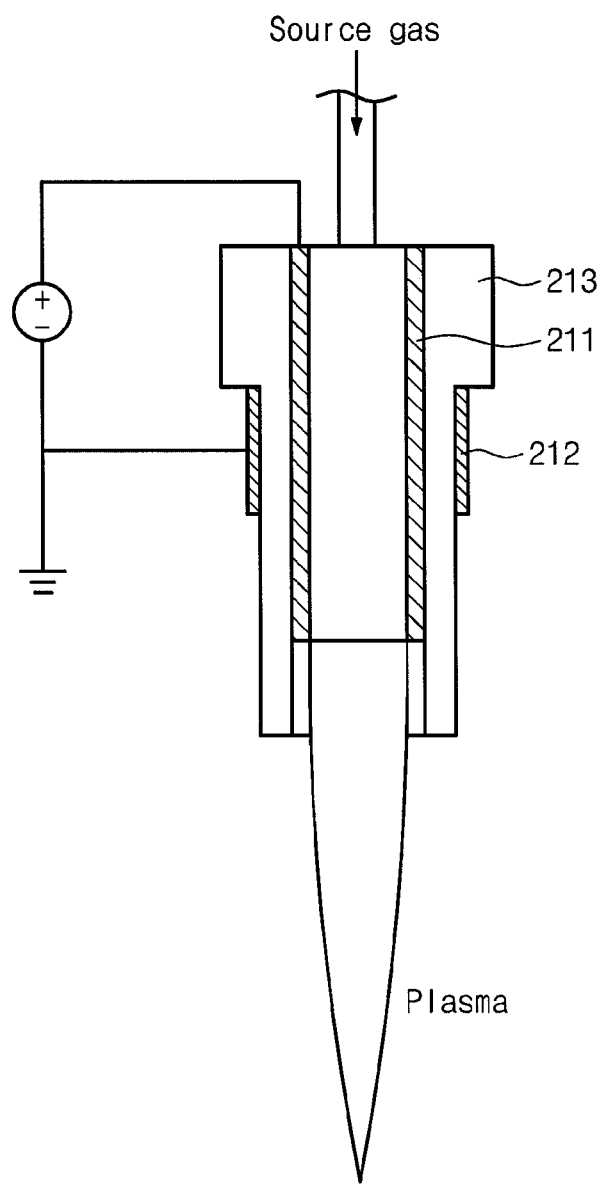
FIG. 30 is a sectional view illustrating a plasma generation unit according to an embodiment of the inventive concept.

FIG. 30 is a sectional view illustrating the plasma generation unit 21 according to an embodiment of the inventive concept.

According to an embodiment of the inventive concept, the plasma generation unit 21 may include a first electrode 211 having an empty space through which the source gas passes, a dielectric material 213 surrounding the first electrode 211, and a second electrode 212 surrounding at least part of the dielectric material 213.

For example, as illustrated in FIG. 30, the first and second electrodes 211 and 212 may face each other with the dielectric material 213 therebetween. Here, the second electrode 212 on the outside of the plasma generation unit 21 may be disposed to surround a partial area of the first electrode 211 inside the plasma generation unit 21.

That is, the first electrode 211 and the second electrode 212 have hollow cylindrical shapes with different diameters and lengths and are disposed to overlap each other with the dielectric material 213 therebetween. However, the area of the first electrode 211 that overlaps the second electrode 212 is a partial area of the first electrode 211.

Furthermore, the plasma treatment apparatus 2 further includes a power supply that supplies power for generating plasma to the plasma generation unit 21.

Referring to FIG. 30, the power supply may apply a power signal to the first electrode 211 and may ground the second electrode 212. The power supply may apply a high-voltage direct current signal or a high-frequency signal as the power signal.

According to an embodiment of the inventive concept, the gas supply unit may supply an inert gas to the plasma generation unit 21 as the source gas. For example, the gas supply unit may supply at least one of argon and helium. In the case where the inert gas such as argon or helium is supplied as the source gas, ozone harmful to a human body may be minimized when plasma is generated.

Referring again to FIG. 29, the path-providing unit 23 provides a path along which the plasma generation unit 21 moves above the body part to be treated.

Although not illustrated in FIG. 29, the path-providing unit 23 may include a rail that supports a wheel included in the plasma generation unit 21. In this case, the wheel included in the plasma generation unit 21 may rotates on the rail, and therefore the plasma generation unit 21 may move along the rail.

Figure 31:
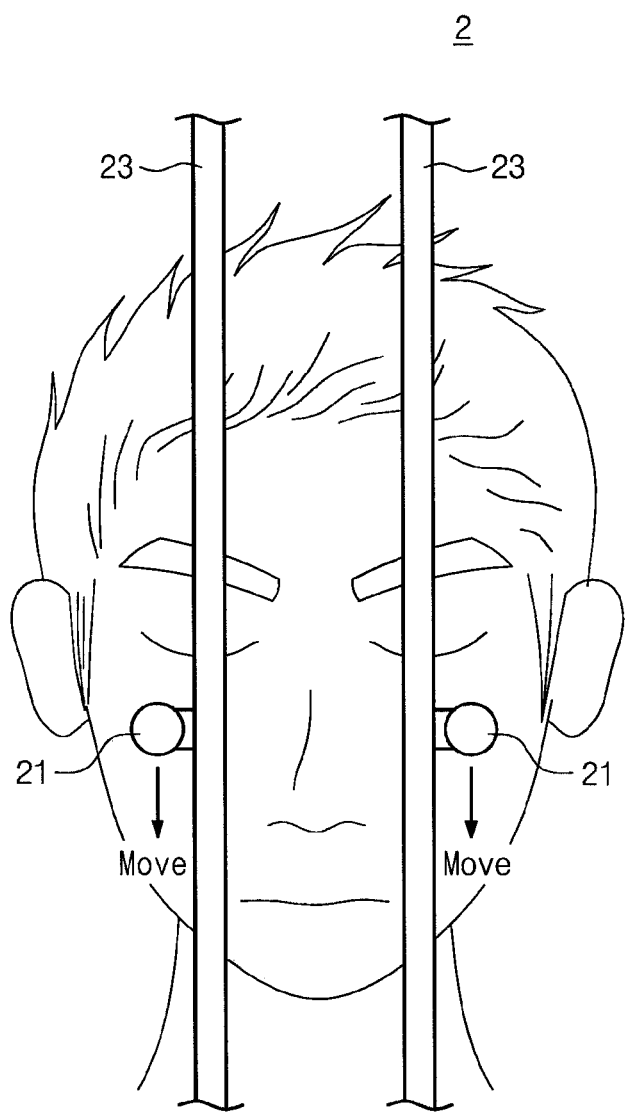
FIGS. 31 and 32 are plan views illustrating the plasma treatment apparatus including a path-providing unit according to an embodiment of the inventive concept.
Figure 32:
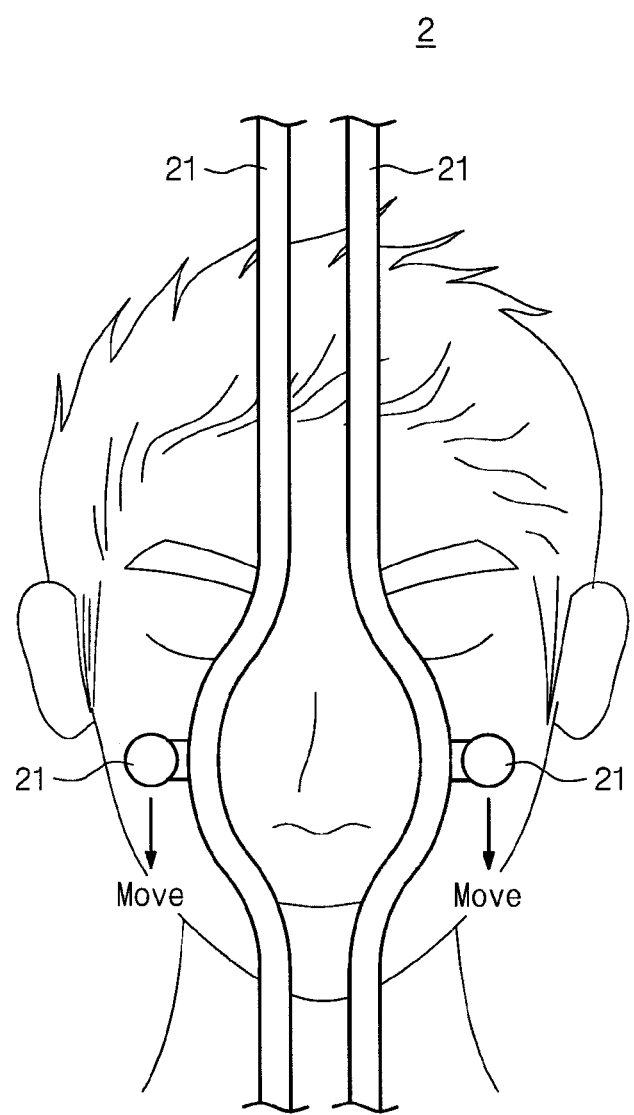

FIGS. 31 and 32 are plan views illustrating the plasma treatment apparatus 2 including the path-providing unit 23 according to an embodiment of the inventive concept.

According to an embodiment of the inventive concept, the path-providing unit 23 may provide a linear path that linearly extends above the body part.

For example, as illustrated in FIG. 31, the path-providing unit 23 may include a linear rail that extends in a straight line. In the case where the body part to be treated with plasma is too wide like a face to be treated with one rail, the path-providing unit 23 may include two or more rails to increase the area to which plasma is provided by the plasma generation unit 21.

In another example, as illustrated in FIG. 32, the path-providing unit 23 may include a curved rail that extends in a curve. In other words, the path provided by the path-providing unit 23 includes a curved path as well as a linear path.

In the case where the path-providing unit 23 provides a curved path above the body part, the curvature or length of the path may be determined and manufactured in advance to be appropriate for the body part to be treated with plasma.

Figure 33:
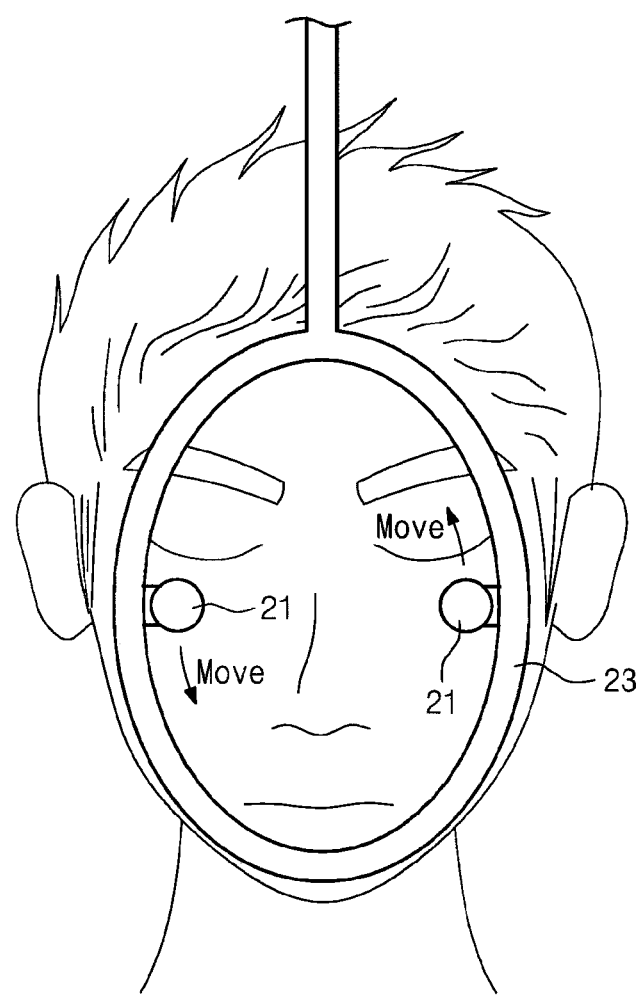
FIG. 33 is a plan view illustrating the plasma treatment apparatus including a path-providing unit according to another embodiment of the inventive concept.

FIG. 33 is a plan view illustrating the plasma treatment apparatus 2 including the path-providing unit 23 according to another embodiment of the inventive concept.

According to another embodiment of the inventive concept, the path-providing unit 23 may provide a loop path that extends in a loop shape above the body part.

For example, referring to FIG. 33, the path-providing unit 23 may include a loop rail with a loop shape. That is, unlike the above-described path-providing unit 23 including the linear rail, the path-providing unit 23 in this embodiment includes a closed loop rail. Likewise to the linear rail, the loop rail may also have a shape or size determined in advance to be appropriate for the body part to be treated with plasma.

FIG. 33 illustrates an example that two plasma generation units 21 provide plasma to a face while moving along the loop rail disposed above the face. Without being limited thereto, however, the number of plasma generation units 21 moving along the loop rail may be one or three or more according to embodiments.

Figure 34:
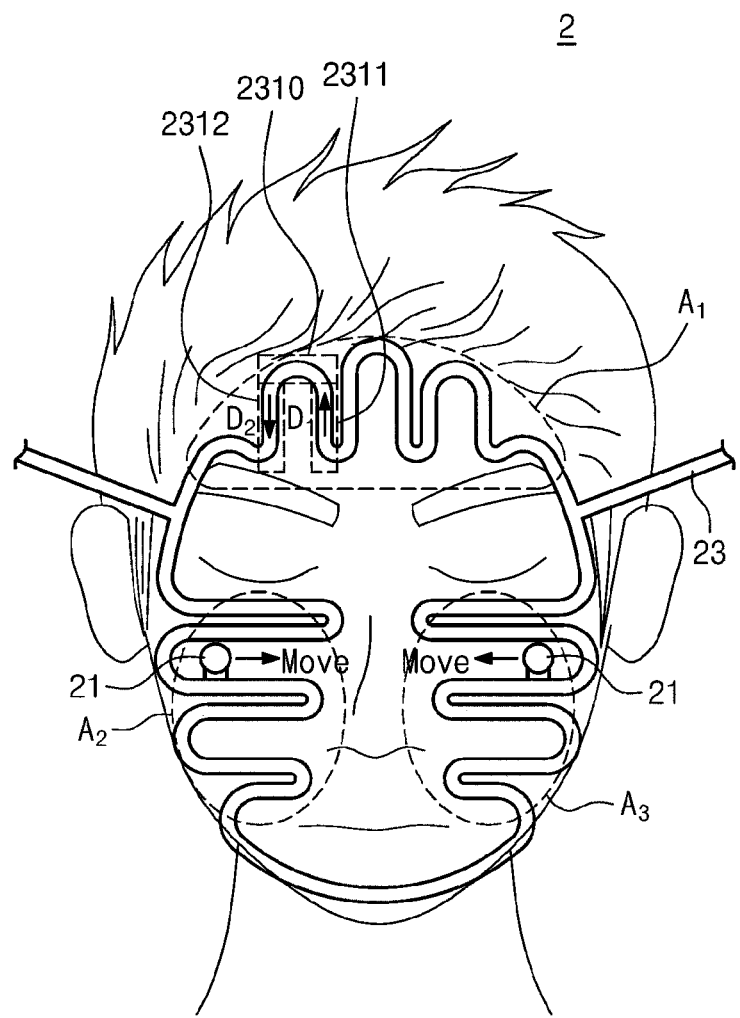
FIG. 34 is a plan view illustrating the plasma treatment apparatus including a path-providing unit according to yet another embodiment of the inventive concept.

FIG. 34 is a plan view illustrating the plasma treatment apparatus 2 including the path-providing unit 23 according to yet another embodiment of the inventive concept.

According to yet another embodiment of the inventive concept, the path-providing unit 23 may provide an intensive care area path in which a first partial path, a turning path, and a second partial path are successively connected.

For example, referring to FIG. 34, the path-providing unit 23 may provide, above one or more predetermined intensive care areas $A_1$, $A_2$, and $A_3$ of the body part, an intensive care area path in which a first partial path 2311 extending in a first direction $D_1$, a turning path 2310 that turns in a second direction $D_2$ opposite to the first direction $D_1$, and a second partial path 2312 extending in the second direction $D_2$ are successively connected.

In this embodiment, the intensive care areas $A_1$, $A_2$, and $A_3$ may be parts to which plasma is intensively provided for treatment, and may correspond to affected parts where acne, an atopic skin disease, a wound, and the like are located. The body part to be treated with plasma in FIG. 34 is a face, and the intensive care areas $A_1$, $A_2$, and $A_3$ are the forehead and the cheeks. However, the sizes and number of the intensive care areas $A_1$, $A_2$, and $A_3$ may be determined in advance based on the location of the body part to be treated with plasma, or the location and size of an affected part in the body part.

As described above, the path-providing unit 23 may provide, above an affected part that has to be intensively treated, the intensive care area path in which the first partial path 2311, the turning path 2310, and the second partial path 2312 are successively connected, thereby enabling the plasma generation unit 21 to intensively provide plasma to a local part of a body for a long time.

Figure 35:
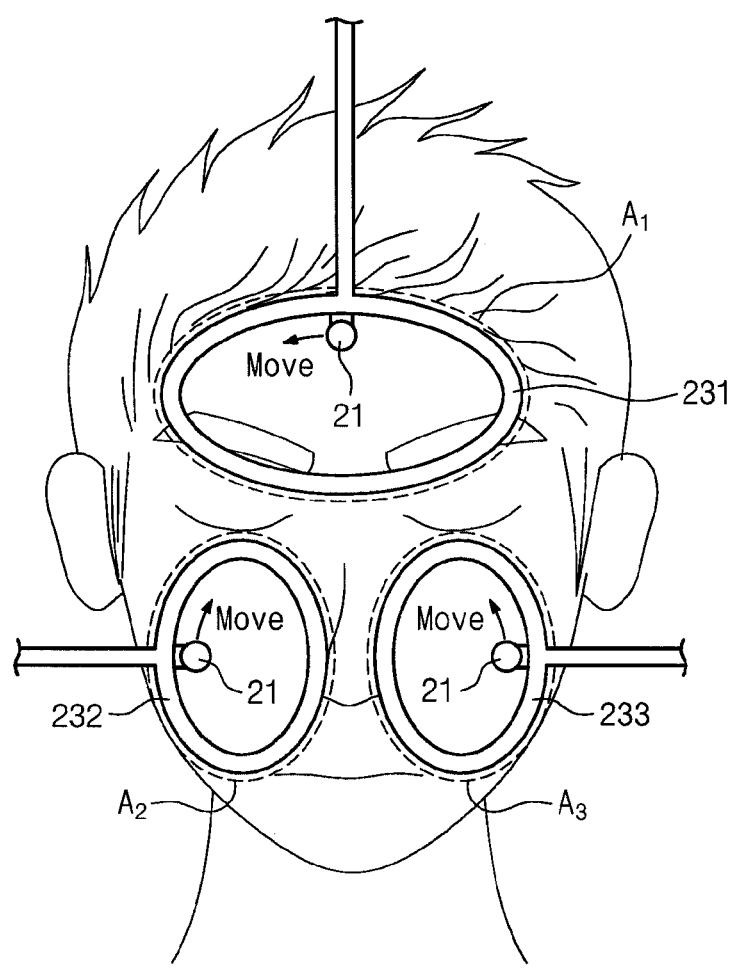
FIG. 35 is a plan view illustrating the plasma treatment apparatus including a path-providing unit according to yet another embodiment of the inventive concept.

FIG. 35 is a plan view illustrating the plasma treatment apparatus 2 including the path-providing unit 23 according to yet another embodiment of the inventive concept.

According to yet another embodiment of the inventive concept, the path-providing unit 23 may provide closed loop paths 231, 232, and 233 to a plurality of predetermined intensive care areas $A_1$, $A_2$, and $A_3$ of the body part, respectively. That is, the path-providing unit 23 in this embodiment provides, above the intensive care areas $A_1$, $A_2$, and $A_3$, the loop paths 231, 232, and 233 instead of a crooked intensive care area path.

The sizes and shapes of the loop paths 231, 232, and 233 may be determined in advance based on the sizes and shapes of the intensive care areas $A_1$, $A_2$, and $A_3$ that have to be intensively treated.

The plasma generation unit 21 may be provided on the loop paths 231, 232, and 233 to consistently provide plasma to a local part of a body while circulating the intensive care areas $A_1$, $A_2$, and $A_3$ along the paths.

Figure 36:
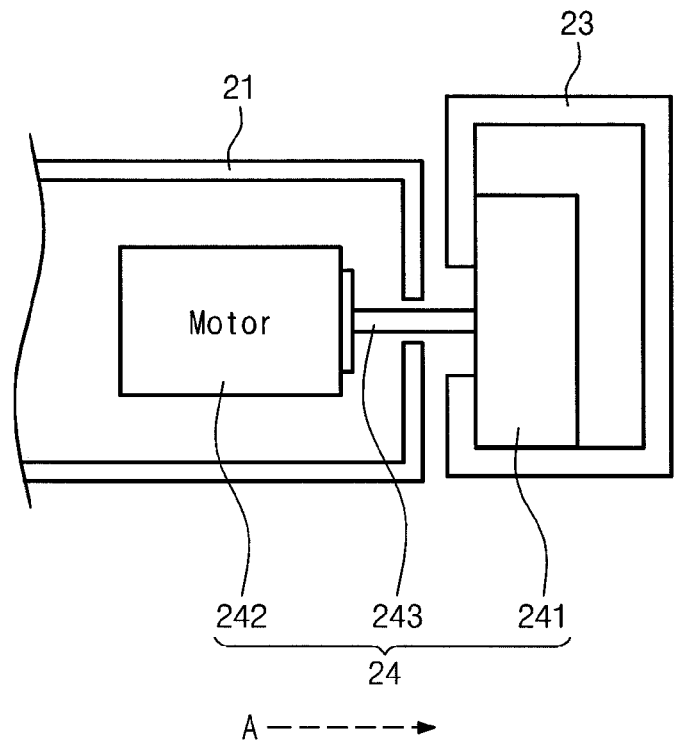
FIG. 36 is a sectional view illustrating a path-providing unit and a driving unit according to an embodiment of the inventive concept.
Figure 37:
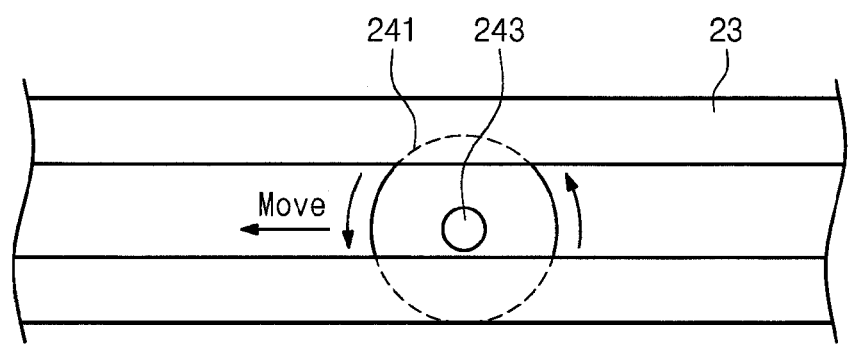
FIG. 37 is a side view illustrating the path-providing unit and a wheel according to an embodiment of the inventive concept, when viewed in the direction A of FIG. 36.

FIG. 36 is a sectional view illustrating the path-providing unit 23 and the driving unit 24 according to an embodiment of the inventive concept, and FIG. 37 is a side view illustrating the path-providing unit 23 and a wheel 241 according to an embodiment of the inventive concept, when viewed in the direction A of FIG. 36.

As described above, the driving unit 24 moves the plasma generation unit 21 along the path-providing unit 23.

According to an embodiment, the driving unit 24 may include the wheel 241 and a motor 242. The wheel 241 is included in the plasma generation unit 21 and supported by the path-providing unit 23. The motor 242 is included in the plasma generation unit 21 to rotate the wheel 241.

Referring to FIG. 36, the plasma generation unit 21 may include the motor 242, and the wheel 241 may be coupled to a rotary shaft 243 extending from the motor 242. The wheel 241 may be coupled to the inside of the rail of the path-providing unit 23 and may be supported by at least one surface of the rail.

According to this embodiment, as the motor 242 operates, the wheel 241 coupled to the rotary shaft 243 rotates, and as the wheel 241 rotates as illustrated in FIG. 37, the plasma generation unit 21 moves along the rail together with the wheel 241.

In this embodiment, the driving unit 24 moves the plasma generation unit 21 along the path-providing unit 23 by using the wheel 241 and the motor 242. However, the technical idea that the driving unit 24 employs to move the plasma generation unit 21 is not limited thereto. The driving unit 24 may move the plasma generation unit 21 along the path-providing unit 23 through various types of means.

Figure 38:
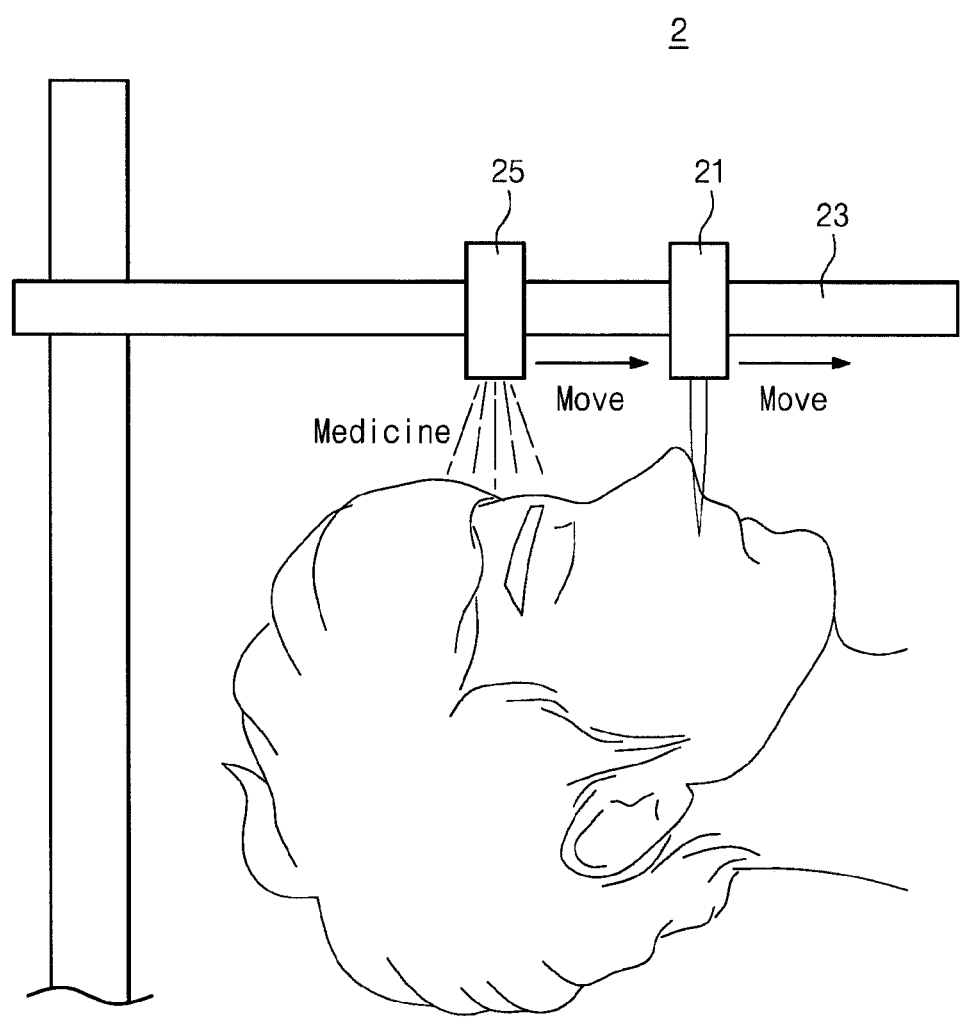
FIG. 38 is a side view illustrating a plasma treatment apparatus according to another embodiment of the inventive concept.
Figure 39:
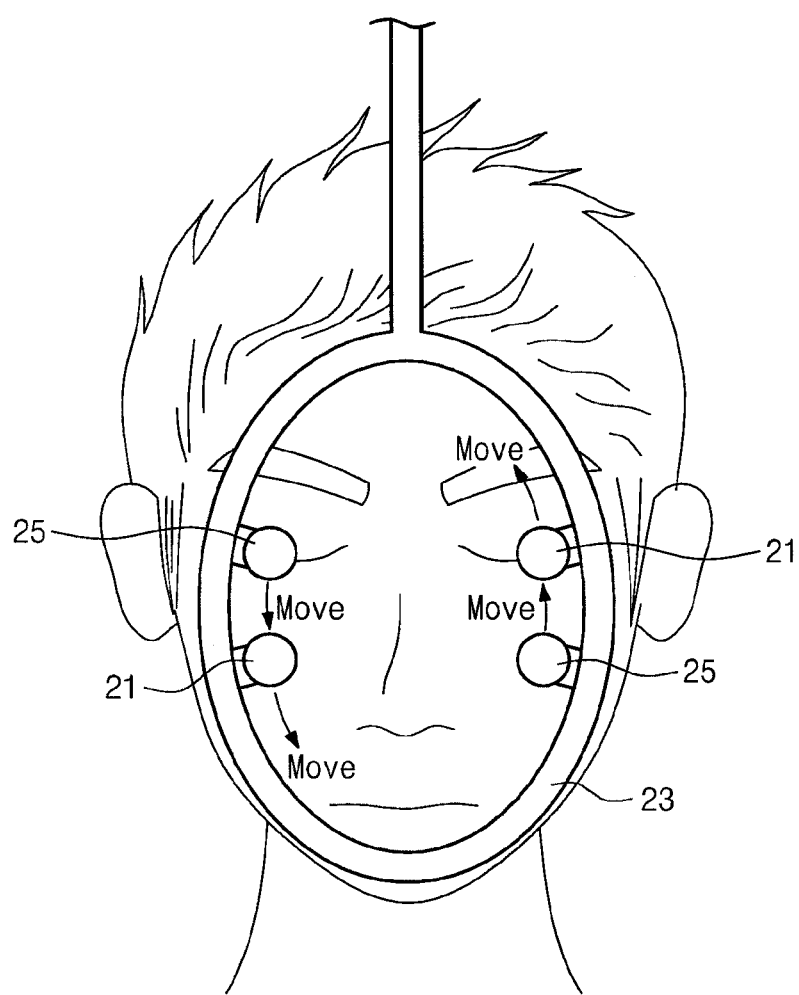
FIG. 39 is a plan view illustrating the plasma treatment apparatus according to another embodiment of the inventive concept.

FIG. 38 is a side view illustrating the plasma treatment apparatus 2 according to another embodiment of the inventive concept, and FIG. 39 is a plan view illustrating the plasma treatment apparatus 2 according to another embodiment of the inventive concept.

According to another embodiment of the inventive concept, the plasma treatment apparatus 2 may further include a medicine spray unit 25. The medicine spray unit 25 sprays a medicine while moving along the path-providing unit 23.

For example, as illustrated in FIGS. 38 and 39, the medicine spray unit 25 following the plasma generation unit 21 may spray the medicine to a body part after the plasma generation unit 21 provides plasma to the body part.

Since the medicine spray unit 25 sprays the medicine after the plasma generation unit 21 provides the plasma to the body part, treatments using the plasma and the medicine may be performed together.

In the case where the path-providing unit 23 provides a linear path above the body part as illustrated in FIG. 38, movement of the plasma generation unit 21 and the medicine spray unit 25 may be limited, and operation control (stopping, turning, or the like) thereof may be complicated. However, in the case where the path-providing unit 23 provides a closed loop path as illustrated in FIG. 39, the plasma generation unit 21 and the medicine spray unit 25 may consistently supply the plasma and the medicine to the body part without separate control as long as the plasma generation unit 21 and the medicine spray unit 25 move at the same speed so as not to collide with each other.

Figure 40:
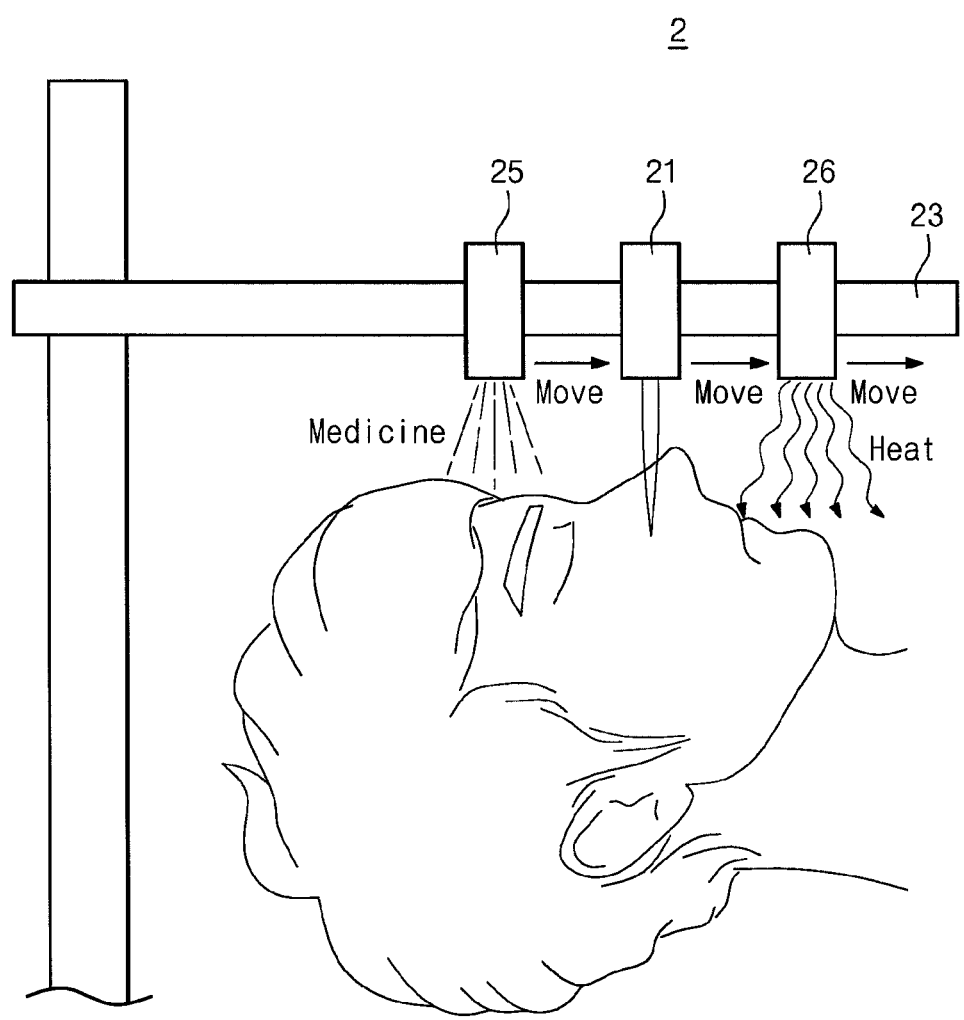
FIG. 40 is a side view illustrating a plasma treatment apparatus according to yet another embodiment of the inventive concept.
Figure 41:
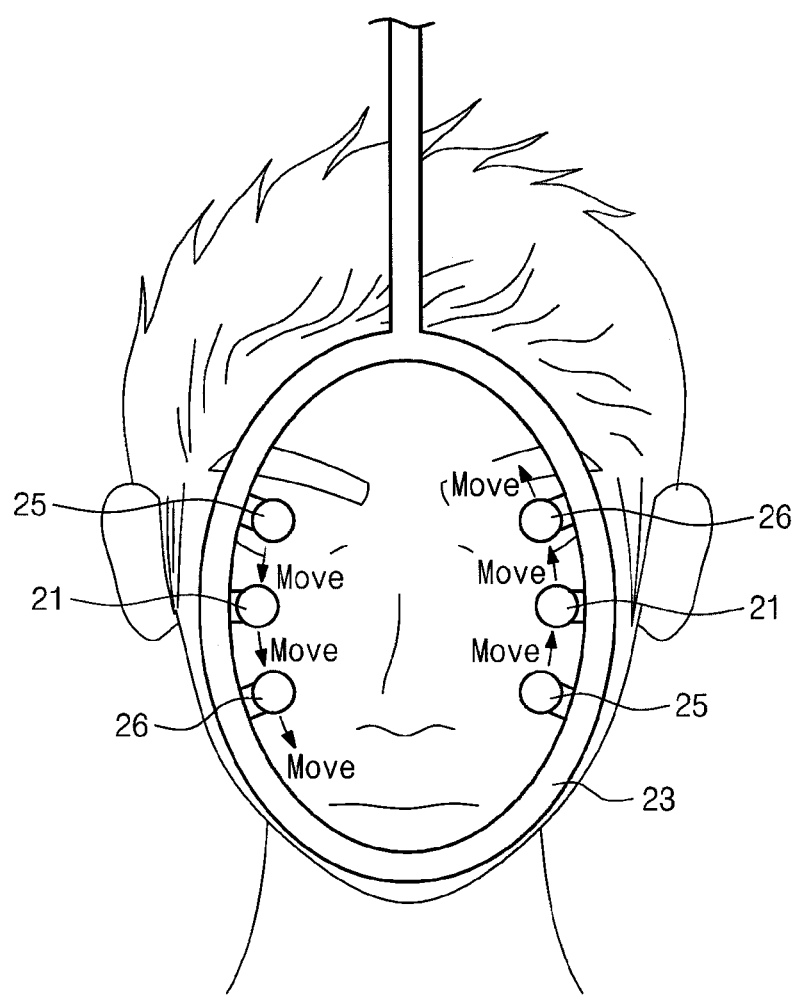
FIG. 41 is a plan view illustrating the plasma treatment apparatus according to yet another embodiment of the inventive concept.

FIG. 40 is a side view illustrating the plasma treatment apparatus 2 according to yet another embodiment of the inventive concept, and FIG. 41 is a plan view illustrating the plasma treatment apparatus 2 according to yet another embodiment of the inventive concept.

According to yet another embodiment of the inventive concept, the plasma treatment apparatus 2 may further include a heater 26. The heater 26 radiates heat while moving along the path-providing unit 23.

For example, as illustrated in FIGS. 40 and 41, the heater 26 ahead of the plasma generation unit 21 may transfer heat to a body part before the plasma generation unit 21 provides plasma to the body part.

As a result, the temperature of skin may be raised by heating before plasma and a medicine are provided to the body part, and therefore the action of the plasma on the body part and the absorption of the medicine may be promoted, thereby improving treatment effects.

Likewise to the plasma generation unit 21, the medicine spray unit 25 and the heater 26 also move along the path-providing unit 23. Accordingly, a component similar to the driving unit 24 described above may be applied to the medicine spray unit 25 and the heater 26 to move the medicine spray unit 25 and the heater 26 along the rail.

Figure 42:
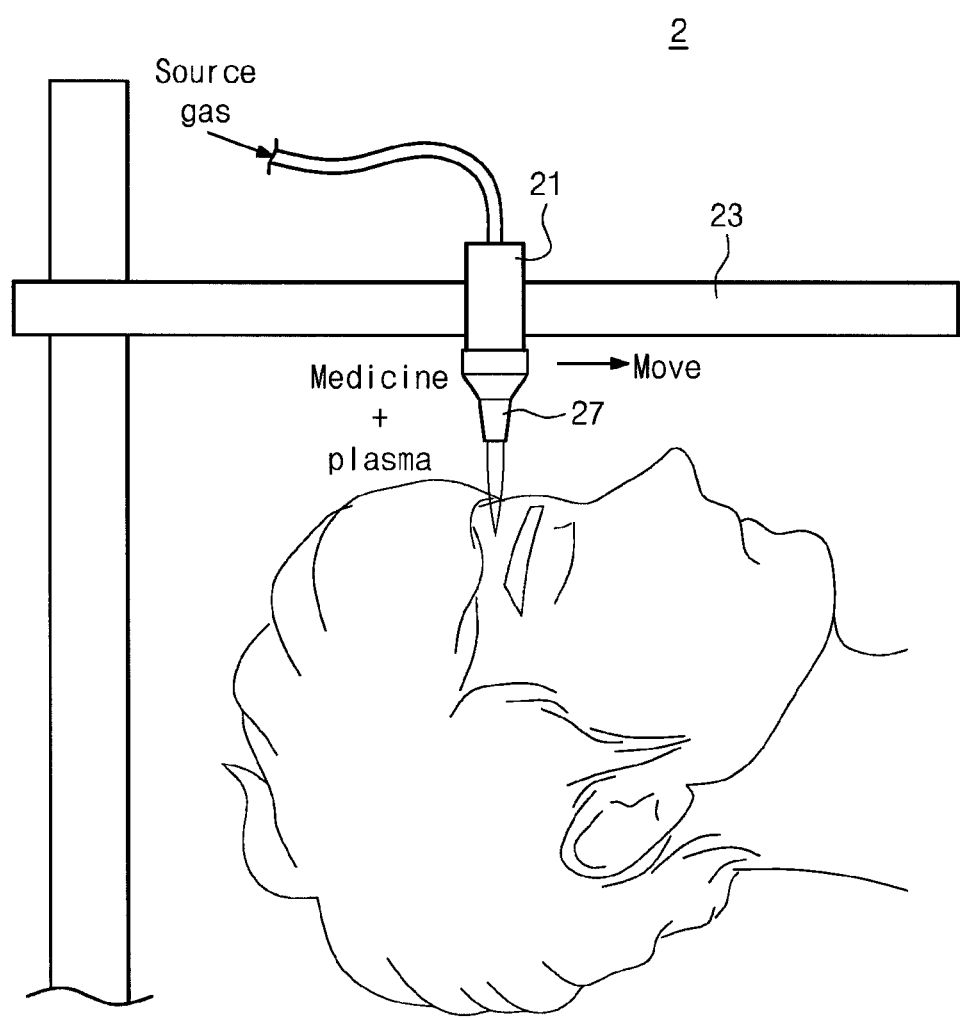
FIG. 42 is a side view illustrating a plasma treatment apparatus according to yet another embodiment of the inventive concept.

FIG. 42 is a side view illustrating the plasma treatment apparatus 2 according to yet another embodiment of the inventive concept.

According to yet another embodiment of the inventive concept, the plasma treatment apparatus 2 may further include a medicine mixing unit 27. The medicine mixing unit 27 having a medicine received therein is fastened to the plasma generation unit 21 to mix the medicine with plasma.

Figure 45:
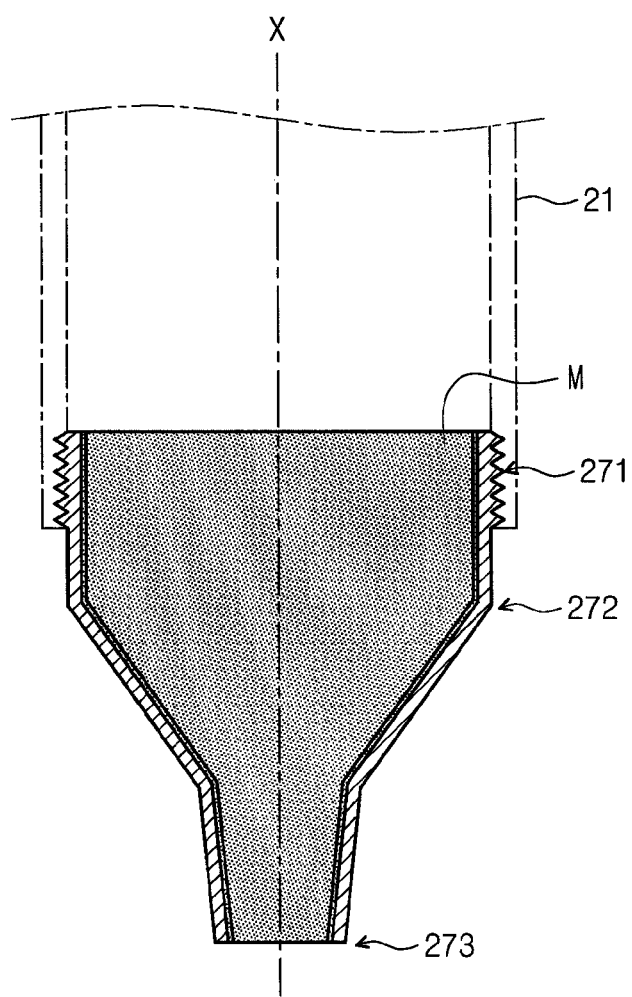
FIGS. 45 and 46 are a sectional view and a side view illustrating the medicine mixing unit according to an embodiment of the inventive concept.

For example, as illustrated in FIG. 45, the medicine mixing unit 27 may be fastened to a nozzle through which plasma is discharged from the plasma generation unit 21. Since the medicine mixing unit 27 has the medicine received therein and is fastened to the plasma generation unit 21, the plasma generation unit 21 may provide, to a body part, plasma mixed with the medicine through the medicine mixing unit 27.

Hereinafter, embodiments of the medicine mixing unit 27 will be described in detail with reference to drawings.

Figure 43:
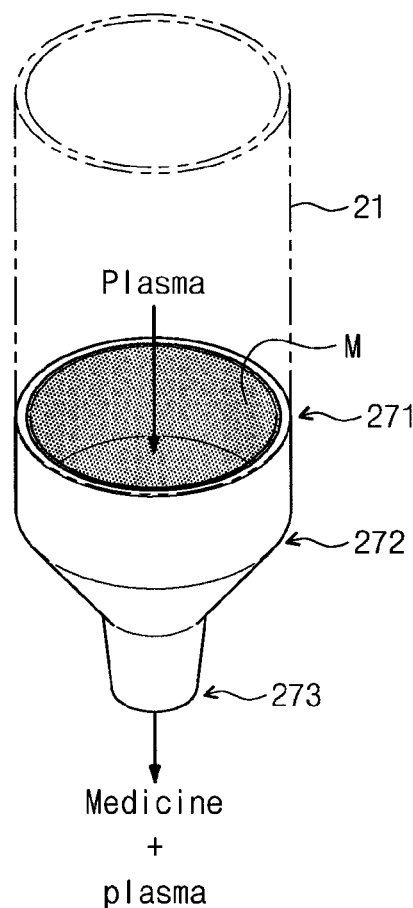
FIGS. 43 and 44 are a perspective view and a sectional view illustrating a medicine mixing unit according to an embodiment of the inventive concept.
Figure 44:
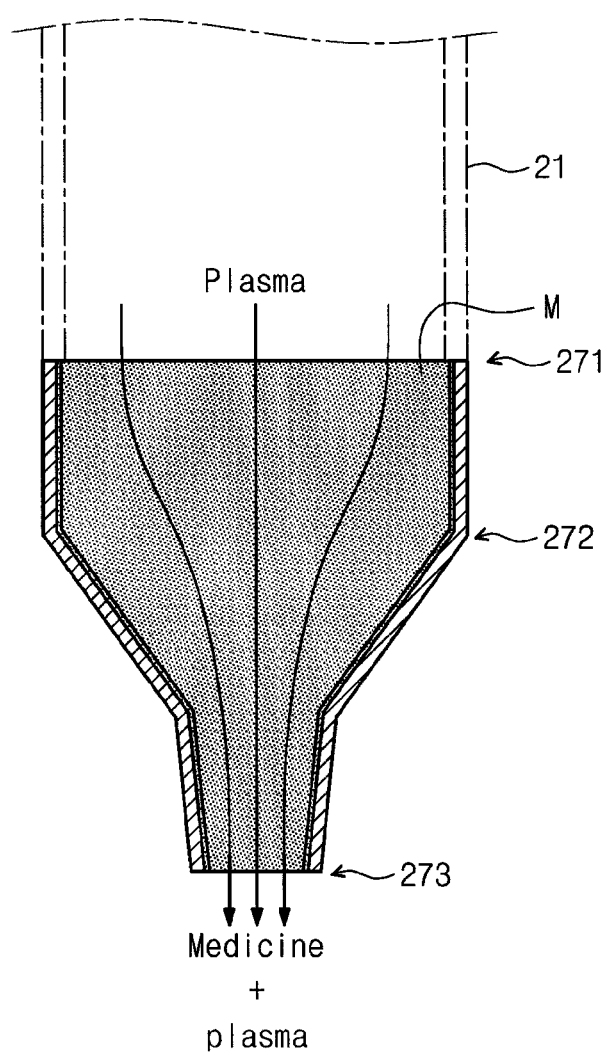

FIGS. 43 and 44 are a perspective view and a sectional view illustrating the medicine mixing unit 27 according to an embodiment of the inventive concept.

The medicine mixing unit 27 according to an embodiment of the inventive concept is a member attached to the plasma generation unit 21 to further enhance unique actions of plasma. The medicine mixing unit 27 has a medicine M for enhancing actions of plasma and provides plasma mixed with the medicine M.

Referring to FIGS. 43 and 44, the medicine mixing unit 27 includes a fastening part 271 coupled to the plasma generation unit 21, a medicine receiving part 272 that receives the medicine M for enhancing actions of plasma, and a discharging part 273 that discharges plasma including the medicine M.

The fastening part 271 may be fastened to the nozzle through which plasma is discharged from the plasma generation unit 21. Since the fastening part 271 is fastened to an end portion of the nozzle of the plasma generation unit 21, plasma generated by the plasma generation unit 21 is discharged to the outside along with the medicine M past the medicine mixing unit 27.

Figure 46:
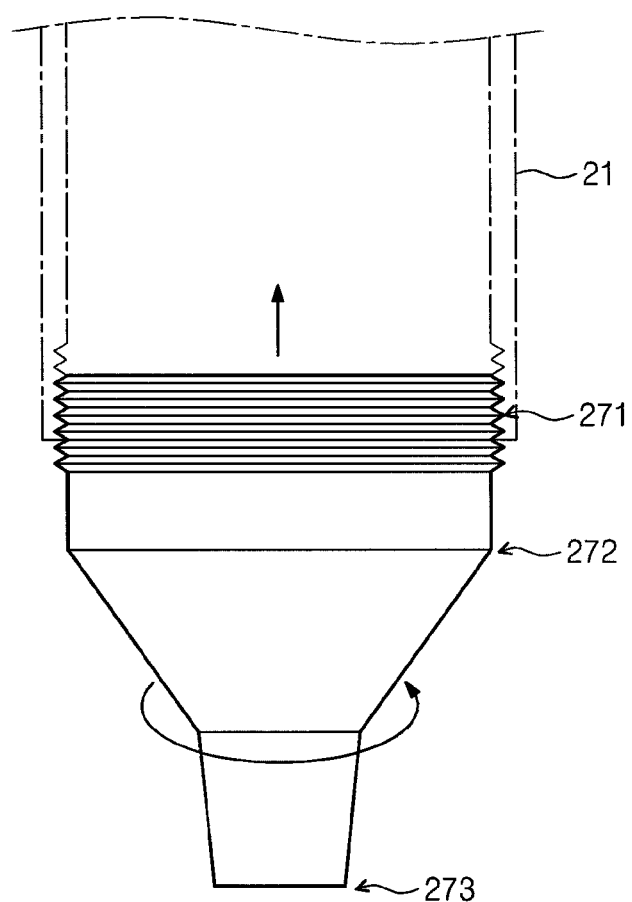

FIGS. 45 and 46 are a sectional view and a side view illustrating the medicine mixing unit 27 according to an embodiment of the inventive concept.

According to an embodiment of the inventive concept, the fastening part 271 may be screw-coupled to the nozzle of the plasma generation unit 21. As illustrated in FIG. 45, for the screw-coupling of the fastening part 271 and the nozzle of the plasma generation unit 21, the nozzle and the fastening part 271 have threads engaged with each other.

In addition, according to this embodiment, the fastening part 271 may be coupled to a thread formed on the nozzle, the pitch of which is formed in a direction parallel to a nozzle axis X. In other words, as illustrated in FIG. 45, the pitch of the thread formed on the nozzle may extend in the direction of the nozzle axis X.

Due to the above-described structure, a user, as illustrated in FIG. 46, may rotate the medicine mixing unit 27 about the nozzle axis X to adjust the degree to which the medicine mixing unit 27 protrudes. According to this embodiment, in the case where the length of a plasma jet discharged from the discharging part 273 of the medicine mixing unit 27 is restricted and the distance between a target part (e.g., a body part) to which plasma is applied and the medicine mixing unit 27 is not constant, the user may adjust the degree to which the medicine mixing unit 27 protrudes toward the target part, thereby effectively applying plasma to the target part.

The medicine receiving part 272 receives the medicine M for enhancing actions of plasma.

For example, as illustrated in FIGS. 43 to 45, the medicine M may be applied to the inner surface of the medicine mixing unit 272, and plasma passing through the medicine receiving part 272 may be mixed with the medicine M.

Figure 47:
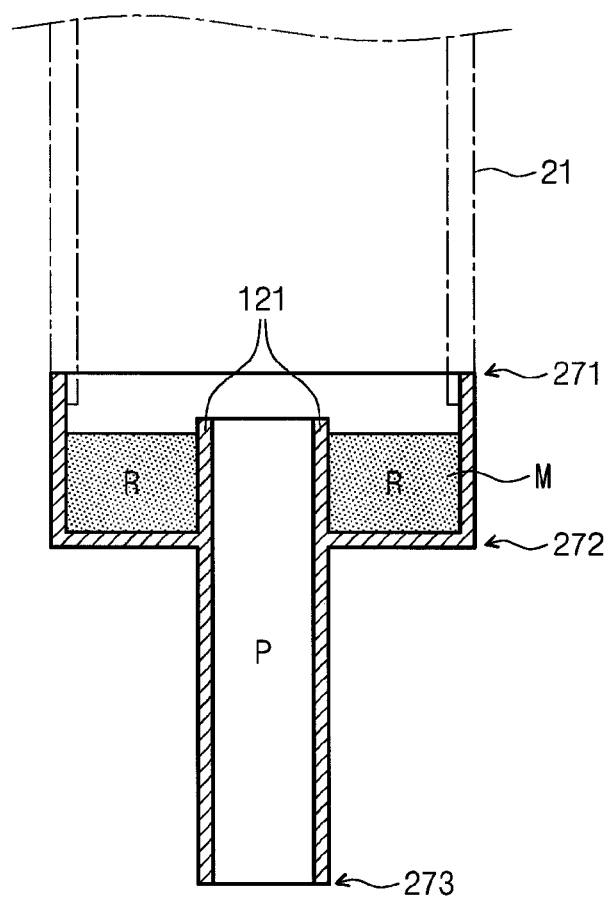
FIGS. 47 to 49 are sectional views illustrating medicine receiving parts and medicines M received therein according to embodiments of the inventive concept.
Figure 48:
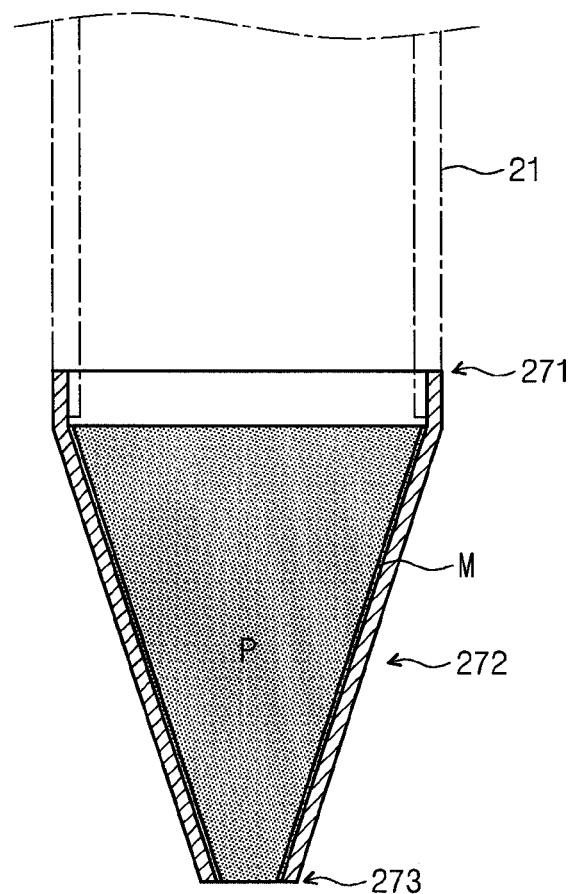
Figure 49:
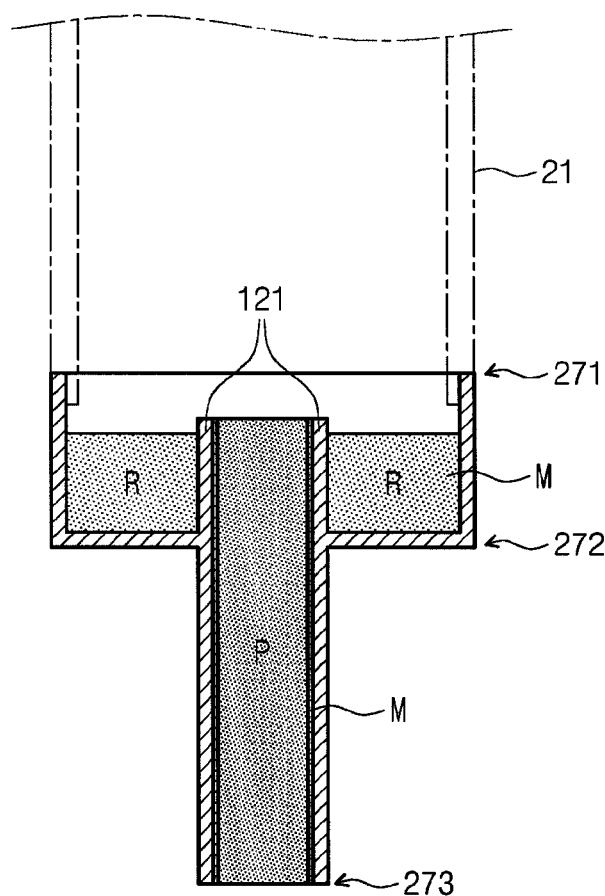

FIGS. 47 to 49 are sectional views illustrating the medicine receiving part 272 and the medicine M received therein according to embodiments of the inventive concept.

According to an embodiment of the inventive concept, the medicine receiving part 272 may be formed inside the medicine mixing unit 27 and may receive the medicine M in a space R formed on a transfer path P for transferring plasma from the plasma generation unit 21 to the discharging part 273.

That is, the medicine mixing unit 27 in this embodiment may be configured to ensure the space R with a predetermined size on the transfer path P through which plasma passes, and the medicine M may be received in the space R.

According to an embodiment, as illustrated in FIG. 47, the space R and the transfer path P may be distinguished from each other with a partition wall 221 therebetween. In this case, the medicine M may be received between the partition wall 221 and an inner wall of the medicine receiving part 272.

According to another embodiment of the inventive concept, the medicine receiving part 272 may be formed inside the medicine mixing unit 27 and may receive the medicine M on the transfer path P for transferring plasma from the plasma generation unit 21 to the discharging part 273.

For example, referring to FIG. 48, the medicine mixing unit 27 may have a tapered shape that becomes gradually narrower toward one end, and the medicine M may be applied to the surface of the transfer path P formed in the medicine mixing unit 27.

Furthermore, according to yet another embodiment of the inventive concept, the medicine receiving part 272 may receive the medicine M in both the transfer path P and the space R formed on the transfer path.

For example, referring to FIG. 49, the medicine mixing unit 27 may be configured to have both the transfer path P and the space R, and the medicine M may fill the space R and may be coated on the transfer path P.

According to an embodiment of the inventive concept, the medicine receiving part 272 may receive hydrogen peroxide as the medicine M. In the case where hydrogen peroxide with a predetermined concentration is used as the medicine M, germicidal action of plasma may be significantly enhanced than in the case where only plasma is used. However, the medicine M is not limited to hydrogen peroxide, and various materials may be used as the medicine M, depending on a treatment purpose or a part to be treated.

According to an embodiment, the transfer path P may include a straight tube that extends from the nozzle in a straight line. For example, the transfer path P in FIGS. 47 and 49 is a straight tube with a constant diameter, and the transfer path P in FIG. 48 is a straight tube with a variable diameter in the lengthwise direction.

However, according to an embodiment, the transfer path P may include a curved tube or a bent tube other than the straight tube.

Figure 50:
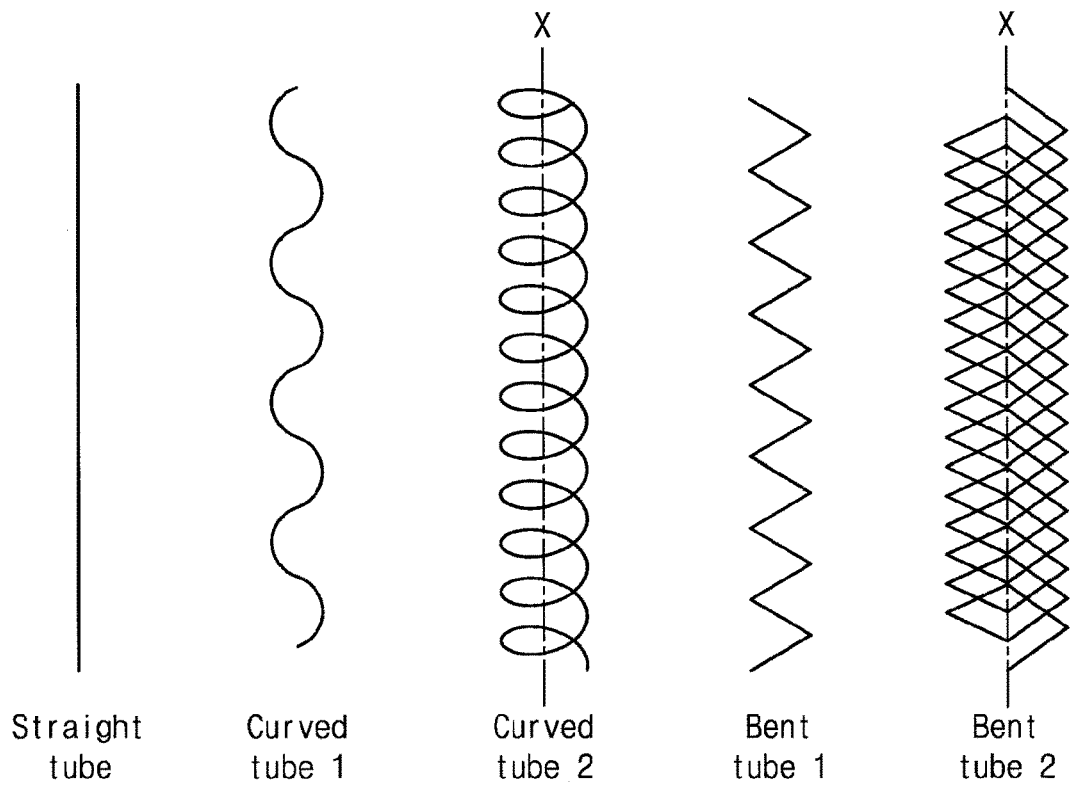
FIG. 50 is a schematic view illustrating transfer paths according to various embodiments of the inventive concept.

FIG. 50 is a schematic view illustrating the transfer path P according to various embodiments of the inventive concept.

In FIG. 50, the transfer path P formed in the medicine mixing unit 27 is represented simply by a solid line, without regard for the thickness of the transfer path P.

As described above, the transfer path P may extend in a straight line from the nozzle of the plasma generation unit 21 to the discharging part 273 of the medicine mixing unit 27 (see a straight tube of FIG. 50).

However, according to another embodiment, the transfer path P may extend in a curve shape from the nozzle to the discharging part 273 (see curved tubes 1 and 2 of FIG. 50).

In this case, the curved tube may extend in a curve shape on a virtual plane where the nozzle and the discharging part 273 are located. That is, likewise to curved tube 1 of FIG. 50, the curved tube may be curved on a single plane.

In another case, the curved tube may be formed to be wound around a virtual line that connects the nozzle and the discharging part 273. That is, likewise to curved tube 2 of FIG. 50, the curved tube may not be located on a single plane and may be formed to be wound around an axis X that connects the nozzle and the discharging part 273.

In addition, according to yet another embodiment, the transfer path P may extend in a broken line shape from the nozzle to the discharging part 273 (see bent tubes 1 and 2 of FIG. 50).

In this case, the bent tube may extend in a broken line shape on a virtual plane where the nozzle and the discharging part 273 are located. That is, likewise to bent tube 1 of FIG. 50, the bent tube may be bent on a single plane.

In another case, the bent tube may be formed to be wound around a virtual line that connects the nozzle and the discharging part 273. That is, likewise to bent tube 2 of FIG. 50, the bent tube may not be located on a single plane and may be formed to be wound in a broken line shape around the axis X that connects the nozzle and the discharging part 273.

Since the curved tube and the bent tube are curved or bent in a direction different from the direction of the axis X that connects the nozzle and the discharging part 273, the curved tube and the bent tube have a longer plasma path than the straight tube. Accordingly, plasma may be mixed with a larger amount of medicine M on the transfer path P, and thus the degree of action of the plasma may be further increased.

Figure 51:
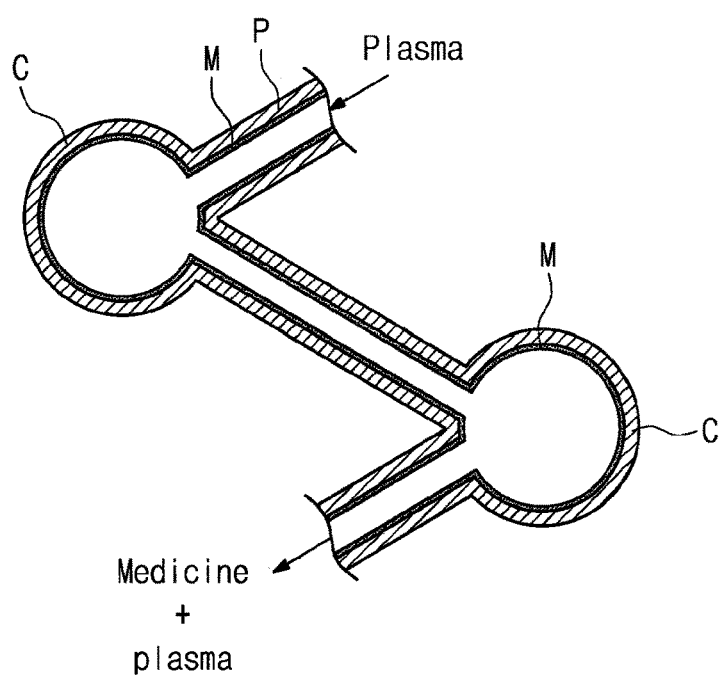
FIG. 51 is a sectional view illustrating a transfer path and a cavity formed therein according to yet another embodiment of the inventive concept.

FIG. 51 is a sectional view illustrating the transfer path P and a cavity C formed therein according to yet another embodiment of the inventive concept.

According to yet another embodiment of the inventive concept, the medicine receiving part 272 may further include, in a portion corresponding to a vertex of a bent tube, the cavity C for receiving a medicine M.

For example, as illustrated in FIG. 51, the bent tube extending in a broken line shape may include the cavity C at the vertex where a straight tube and a straight tube meet. The cavity C may be formed to have a predetermined volume and shape and may receive the medicine M therein. For example, the cavity C may be filled with the medicine M. Without being limited thereto, however, the medicine M may be coated on the inner surface of the cavity C.

According to this embodiment, plasma flowing along the transfer path P may enter the cavity C at the vertex of the bent tube and may form vortex in the cavity C. Accordingly, the plasma may be mixed with a larger amount of medicine M in the cavity C, and thus the degree of action of the plasma may be further increased.

The plasma treatment apparatus 2 described above may treat a body part, such as skin or a wound, using plasma or plasma and a medicine, thereby effectively removing harmful germs in an affected part and promoting regeneration of tissues.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A plasma treatment apparatus comprising:
a cover configured to be attached to a body part;
a plasma generation unit configured to generate plasma and provide the plasma to the cover;
a gas supply unit configured to supply a source gas for generating the plasma to the plasma generation unit;
an exhaust unit configured to exhaust an exhaust gas from the cover;
a by-product removal unit configured to remove a by-product from the exhaust gas;
a sensor unit configured to detect whether the body part is sealed by the cover; and
a controller configured to control the plasma generation unit, depending on whether the body part is sealed or not.

2. The plasma treatment apparatus of claim 1, wherein the plasma generation unit is separated from the cover and provides the plasma to the cover through a tube that connects the plasma generation unit and the cover.

3. The plasma treatment apparatus of claim 1, wherein the plasma generation unit is installed on the cover and provides the plasma into a space between the cover and the body part.

4. The plasma treatment apparatus of claim 3, wherein the plasma generation unit includes opposite electrodes disposed to face each other.

5. The plasma treatment apparatus of claim 4, wherein the plasma generation unit further includes an ozone absorption unit configured to absorb ozone between the opposite electrodes and the space between the cover and the body part.

6. The plasma treatment apparatus of claim 4, wherein the plasma generation unit further includes a medicine supply unit configured to supply a medicine between the opposite electrodes and the space between the cover and the body part.

7. The plasma treatment apparatus of claim 1, wherein a medicine is applied to at least part of one surface of the cover that faces the body part.

8. The plasma treatment apparatus of claim 1, wherein the plasma generation unit is integrated with the cover and generates the plasma in a space between the cover and the body part.

9. The plasma treatment apparatus of claim 8, wherein the plasma generation unit includes:
a first electrode formed on an opposite surface of a dielectric material constituting the cover, the opposite surface being opposite to one surface of the dielectric material that faces the body part; and
a second electrode formed on the one surface of the dielectric material.

10. The plasma treatment apparatus of claim 9, wherein the cover further includes a medicine applied to the one surface of the dielectric material.

11. The plasma treatment apparatus of claim 1, wherein the exhaust unit exhausts air from a space between the cover and the body part before the plasma generation unit generates the plasma after the cover is attached to the body part.

12. The plasma treatment apparatus of claim 1, wherein the sensor unit includes at least one contact sensor provided on a boundary surface of the cover that makes contact with the body part and configured to detect whether the boundary surface and the body part are brought into contact with, or separated from, each other.

13. The plasma treatment apparatus of claim 12, wherein the controller stops an operation of the plasma generation unit when the boundary surface and the body part are separated from each other.

14. The plasma treatment apparatus of claim 13, wherein the controller restarts the operation of the plasma generation unit when the boundary surface and the body part are brought into contact with each other again.

15. The plasma treatment apparatus of claim 12, wherein the exhaust unit includes a variable suction pump configured to take in the exhaust gas from a space between the cover part and the body part, the variable suction pump being variable in suction pressure, wherein when the boundary surface and the body part are separated from each other, the controller raises the suction pressure of the variable suction pump and stops an operation of the variable suction pump after preset time passes.

16. The plasma treatment apparatus of claim 15, wherein the controller restarts the operation of the variable suction pump when the boundary surface and the body part are brought into contact with each other again.

17. The plasma treatment apparatus of claim 12, wherein the cover is configured such that a supply hole through which the cover receives the plasma from the plasma generation unit or receives air from the gas supply unit has a larger area than an exhaust hole through which the exhaust gas is discharged to the exhaust unit.

18. The plasma treatment apparatus of claim 17, wherein the cover further includes an exhaust hole adjustment unit configured to hide or open part of the exhaust hole to adjust the area of the exhaust hole, wherein when the boundary surface and the body part are separated from each other, the controller controls the exhaust hole adjustment unit to open part of the exhaust hole to increase the area of the exhaust hole.

19. The plasma treatment apparatus of claim 18, wherein when the boundary surface and the body part are brought into contact with each other again, the controller controls the exhaust hole adjustment unit to hide part of the exhaust hole to decrease the area of the exhaust hole.

* * * * *